United States Patent
Manuel et al.

(10) Patent No.: US 11,636,929 B2
(45) Date of Patent: Apr. 25, 2023

(54) UPLOADING A DATA RECORD TO A CLOUD REPOSITORY

(71) Applicant: Siemens Healthcare GmbH, Erlangen (DE)

(72) Inventors: Sujith Manuel, Erlangen (DE); Srividya Tirunellai Rajamani, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 300 days.

(21) Appl. No.: 16/640,110

(22) PCT Filed: Aug. 7, 2018

(86) PCT No.: PCT/EP2018/071349
§ 371 (c)(1),
(2) Date: Feb. 19, 2020

(87) PCT Pub. No.: WO2019/042719
PCT Pub. Date: Mar. 7, 2019

(65) Prior Publication Data
US 2021/0134406 A1    May 6, 2021

(30) Foreign Application Priority Data
Aug. 31, 2017  (IN) .............................. 201731030921
Sep. 25, 2017  (EP) ..................................... 17192796

(51) Int. Cl.
*G06F 21/62*        (2013.01)
*H04L 67/10*        (2022.01)
*G16H 10/60*        (2018.01)

(52) U.S. Cl.
CPC .......... *G16H 10/60* (2018.01); *G06F 21/6254* (2013.01); *H04L 67/10* (2013.01)

(58) Field of Classification Search
CPC ...... G16H 10/60; G06F 21/6254; H04L 67/10
See application file for complete search history.

(56) References Cited

U.S. PATENT DOCUMENTS

| | | | |
|---|---|---|---|
| 2007/0027715 A1 | 2/2007 | Gropper et al. | |
| 2013/0208966 A1* | 8/2013 | Zhao | G06Q 40/08 709/219 |

(Continued)

FOREIGN PATENT DOCUMENTS

| | | |
|---|---|---|
| CN | 1961321 A | 5/2007 |
| WO | WO 2013034310 A2 | 3/2013 |
| WO | WO 2013124041 A1 | 8/2013 |

OTHER PUBLICATIONS

Bradley, Malin: Guidance Regarding Methods for De-identification of Protected Health Information in Accordance with the Health Insurance Portability and Accountability Act (HIPAA) Privacy Rule; Nov. 26, 2012; XP055463396; 2012.

(Continued)

*Primary Examiner* — Cheikh T Ndiaye
(74) *Attorney, Agent, or Firm* — Harness, Dickey & Pierce, P.L.C.

(57) ABSTRACT

A method and a local transmission unit are for uploading a data record to a cloud data repository. The method includes receiving a medical data record by a local transmission software, the local transmission software including a core module and available plug-ins, each available plug-in being associated with a remote application. The method further includes generating an anonymized data record based on the medical data record by a processing plug-in, the processing plug-in being one of the available plug-ins. Finally, the method includes uploading the anonymized data record to a cloud data repository, the anonymized data record in the (Continued)

cloud data repository being accessible by the remote application associated with the processing plug-in.

24 Claims, 18 Drawing Sheets

(56) References Cited

U.S. PATENT DOCUMENTS

| | | | | |
|---|---|---|---|---|
| 2013/0263088 | A1* | 10/2013 | Hoff | G06F 8/61 |
| | | | | 717/121 |
| 2014/0275807 | A1* | 9/2014 | Redei | G16H 15/00 |
| | | | | 600/300 |
| 2016/0125138 | A1 | 5/2016 | Dorn et al. | |
| 2016/0148017 | A1* | 5/2016 | Goßler | G06F 21/6254 |
| | | | | 726/27 |
| 2016/0267227 | A1* | 9/2016 | Takeyama | G16H 10/60 |
| 2017/0124464 | A1 | 5/2017 | Crabtree et al. | |
| 2017/0243028 | A1* | 8/2017 | LaFever | G06F 21/6254 |

OTHER PUBLICATIONS

Vladyslav, Ukis et al.: "Architecture of Cloud-Based Advanced Medical Image Visualization Solution"; 2013 IEEE International Conference on Cloud Computing in Emerging Markets (CCEM), IEEE; Oct. 16, 2013; pp. 1-5; XP032531309; DOI: 10.1109/CCEM.2013.6684428; 2013.

Microsoft "Design Guidelines for Developing Class Libraries" 2005 // https://docs.microsoft.com/en-us/previous-versions/dotnet/netframework-4.0/ms229042(v=vs.100)?redirectedfrom=MSDN.

Microsoft "Application domains" Mar. 30, 2017 // https://docs.microsoft.com/en-us/dotnet/framework/app-domains/application-domains?redirectedfrom=MSDN.

International Search Report and Written Opinion dated Nov. 6, 2018.

Extended European Search Report dated Apr. 25, 2018.

* cited by examiner

UPLOADING A DATA RECORD TO A CLOUD REPOSITORY

PRIORITY STATEMENT

This application is the national phase under 35 U.S.C. § 371 of PCT International Application No. PCT/EP2018/071349 which has an International filing date of Aug. 7, 2018, which designated the United States of America and which claims priority to European patent application no. EP 17192796.5 filed Sep. 25, 2017, and India patent application no. 20171030921 filed Aug. 31, 2017, the entire contents of each of which are hereby incorporated herein by reference.

FIELD

Embodiments of the invention generally relate to a method for uploading a data record to a cloud repository; and a local transmission unit for hosting circuitry for uploading a data record to a cloud repository.

BACKGROUND

For applying methods like big data analysis or artificial intelligence within the medical context, in general huge amounts of medical data records are needed. In order to use a high enough number of medical data records, it is not enough to consider only the medical data records of one medical institution (e.g. of one hospital or one group of hospitals), but one has to use the data of a plurality of medical institutions.

The document US 20160125138 A1 teaches a method for evaluating medical data within a cloud application. For example, one can use the cloud application to analyze the average dose applied to patients by computed tomography studies within a single medical institution, and to compare the average dose with all medical institutions in the country. Furthermore one can determine the ratio of studies within the single medical institution where the dose is above a national or institutional threshold.

Once such a cloud infrastructure is established, it can be used for further tasks, e.g. for virtual collaboration (by sharing images among medical professionals) or for business analytics.

As disclosed in the document WO 2013/124041 A1, a common method for gathering the medical data records from the plurality of medical institutions is to upload the medical data records of the single medical institutions to a common cloud storage service and/or to a common cloud data repository. The usage of a cloud storage service has the advantage for the single medical institution that it is scalable without the need of investing in local storage hardware. In the contrary, the person-related data of the medical data has to be protected so that no third party can access the person-related data stored within the cloud even in the case of malfunctions. The document US 20160148017 A1 teaches such methods for protecting person-related data.

It is known to use a receiving or transmitting service or a receiving or transmitting software locally installed as on-premise software in the single medical institutions or on single modalities of the single medical institutions, which is responsible for uploading medical data records to the cloud. The usage of such monolith software lacks flexibility and extensibility. Every time another type of local data source should be used, or every time a cloud application needs a different data format or different data records, the whole monolith application has to be changed and tested again, which is a slow and costly procedure.

SUMMARY

At least one embodiment of the invention provides an extensible and more flexible mechanism for transferring data records from a local data repository to a cloud data repository.

Embodiments of the invention are directed to a method for uploading a data record to a cloud data repository, a local transmission unit, a computer program product and a computer-readable storage medium.

Particularly advantageous embodiments and features of the invention are given by the claims and the description. Features of different claim categories may be combined as appropriate to give further embodiments not described herein.

In the following the solution according to at least one embodiment of the invention is described with respect to the claimed local transmission unit as well as with respect to the claimed method. Features, advantages or alternative embodiments herein can be assigned to the other claimed objects and vice versa. In other words, claims for the local transmission unit can be improved with features described or claimed in the context of the method. In this case, the functional features of the method are embodied by objective units of the local transmission unit.

According to at least one embodiment of the invention, the method for uploading a data record to a cloud data repository comprises the step of receiving a medical data record by a local transmission software, wherein the local transmission software comprises a core module and available plug-ins, wherein each available plug-in of the available plug-ins is associated with a remote application; the step of generating an anonymized data record based on the medical data record by a processing plug-in, wherein the processing plug-in is one of the available plug-ins; and the step of uploading the anonymized data record to a cloud data repository, wherein the anonymized data record in the cloud data repository is accessible by the remote application associated with the processing plug-in. In particular the method for uploading a data record to a cloud data repository is a computer-implemented method.

At least one embodiment of the invention furthermore relates to a method for generating an anonymized data record, comprising:

receiving a medical data record by a local transmission software, wherein the local transmission software comprises a core module and available plug-ins, wherein each available plug-in of the available plug-ins is associated with a remote application; and generating an anonymized data record based on the medical data record by a processing plug-in, wherein the processing plug-in is one of the available plug-ins, and wherein the anonymized data record is configured to be input data for the remote application associated with the processing plug-in.

The invention of at least one embodiment furthermore relates to a local transmission unit configured to host a local transmission software for uploading a data record to a cloud data repository, wherein the local transmission software comprises a core module and available plug-ins, wherein each available plug-in of the available plug-ins is associated with a remote application;

wherein the local transmission unit is configured to receive a medical data record by a local transmission software;

wherein the local transmission unit is configured to generate an anonymized data record based on the medical data record by a processing plug-in, wherein the processing plug-in is one of the available plug-ins;

wherein the local transmission unit is configured to upload the anonymized data record to a cloud data repository by the core module, wherein the anonymized data record in the cloud data repository is accessible by the remote application associated with the processing plug-in.

At least one embodiment of the invention relates in one aspect to a computer program product comprising a local transmission software, the local transmission software being loadable into a memory unit of a local transmission unit, including program code sections to make the local transmission unit execute the method for uploading a data record into a cloud data repository or the method for generating an anonymized data record according to an aspect of at least one embodiment of the invention when the local transmission software is executed in the local transmission unit. In particular, the local transmission software is a computer program product.

At least one embodiment of the invention relates in one aspect to a computer-readable medium, on which program code sections of a local transmission software are saved, the program code sections being loadable into and/or executable in a local transmission unit to make the providing system execute the method for uploading a data record into a cloud data repository or the method for generating an anonymized data record according to an aspect of at least one embodiment of the invention when the program code sections are executed in the local transmission unit.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

DETAILED DESCRIPTION OF THE EXAMPLE EMBODIMENTS

Figure 1:
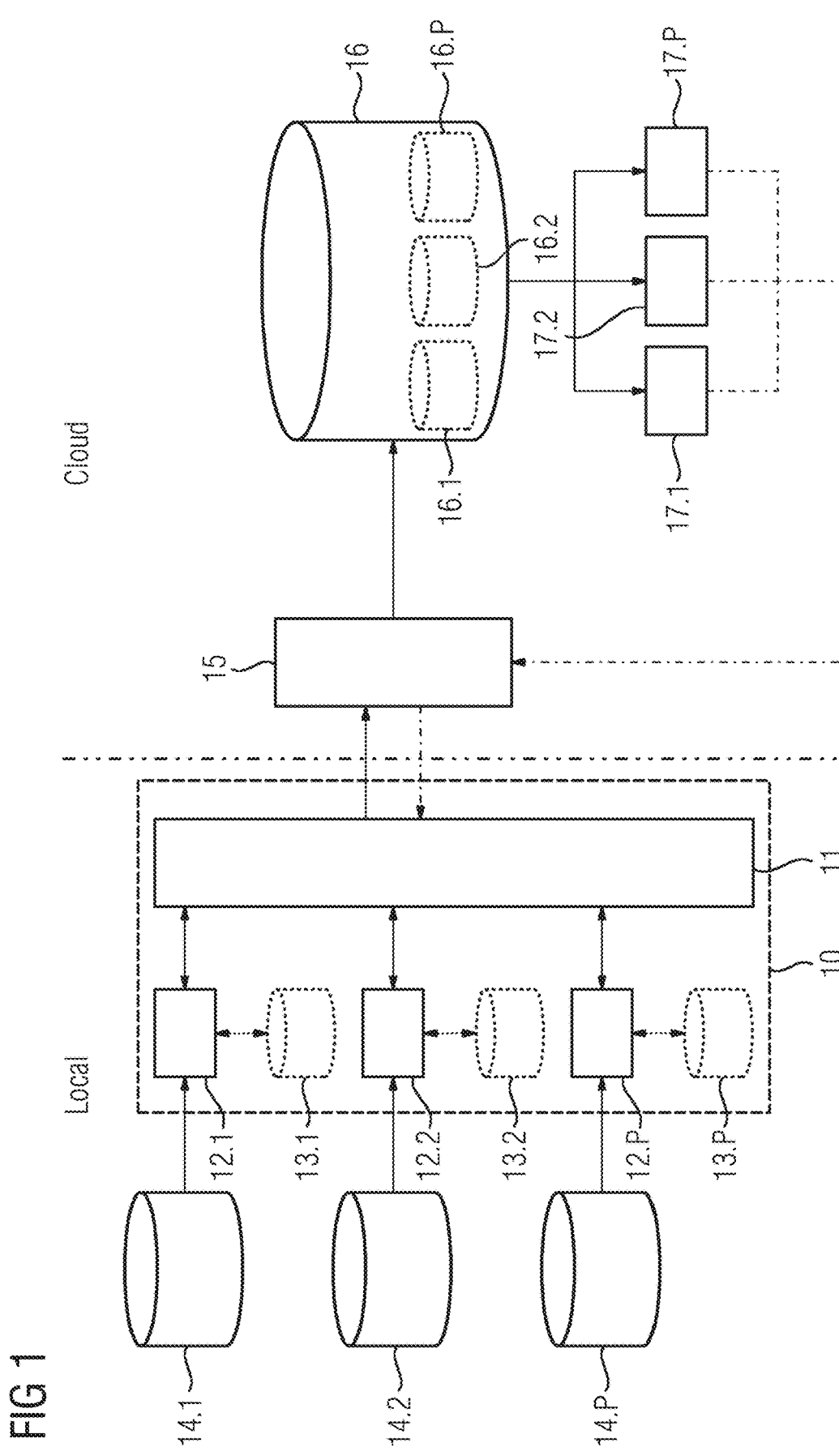
FIG. 1 shows an embodiment of the local transmission software.

According to at least one embodiment of the invention, the method for uploading a data record to a cloud data repository comprises the step of receiving a medical data record by a local transmission software, wherein the local transmission software comprises a core module and available plug-ins, wherein each available plug-in of the available plug-ins is associated with a remote application; the step of generating an anonymized data record based on the medical data record by a processing plug-in, wherein the processing plug-in is one of the available plug-ins; and the step of uploading the anonymized data record to a cloud data repository, wherein the anonymized data record in the cloud data repository is accessible by the remote application associated with the processing plug-in. In particular the method for uploading a data record to a cloud data repository is a computer-implemented method.

An advantage of the method for uploading a data record to a cloud data repository according to at least one embodiment of the invention is that due to the local transmission software comprising a core module and several available plug-ins the functionality of the local transmission software can be easily extended by adding further plug-ins, without changing the core module. As a consequence, only the new plug-in and not the whole local transmission service must be tested, which reduces the costs for the testing procedure.

By performing the anonymization of the medical data record by the processing plug-in, the anonymization can be done more flexible; in particular the anonymization can be coordinated with the needs of the associated remote application. Furthermore it is possible to use different anonymization procedures for different formats of medical data reports (e.g. DICOM or HL7).

According to a further possible aspect of at least one embodiment of the invention, the step of receiving the medical data record comprises checking a local data storage periodical for a new medical data record by the local transmission software, in particular by the core module or the processing plug-in, wherein the new medical data record has not been processed by the local transmission software before, and transmitting the new medical data record from the local data storage to the local transmission software, in particular to the core module or to the processing plug-in. This possible aspect has the advantage that the local data storage must not be adapted to actively send data to the local transmission software, but the standard interface for accessing medical data records within the local data storage can be used by the local transmission software. This reduces costs for altering already existing local data storages.

According to a further aspect of at least one embodiment of the invention, the medical data record is received by the core module, and the method furthermore comprises the step of selecting the processing plug-in from the available plug-ins by the core module based on the medical data record. In particular, the step of selecting the processing plug-in can be based on the local data storage the medical data record originates from. In particular, the step of selecting the processing plug-in can be based on the format of the medical data record. In particular, the step of selecting the processing plug-in can be based on the content of the medical data record. In particular, the step of selecting the processing plug-in can be based on the combination of two or more of the following objects: the local data storage the medical data record originates from, the format of the medical data record, the content of the medical data record. This aspect has the advantage that the local data storages do not need to be adapted to send their data to a specific plug-in, furthermore not every plug-in needs to implement an interface for receiving external data.

According to a further possible aspect of at least one embodiment of the invention, the medical data record is received by the processing plug-in. This possible aspect has the advantage that core module does not need to execute a possibly error-prone selection of the processing module, so that the medical data record is always received by the correct plug-in. In particular a local data storage is configured to send its data directly to one of the plug-ins.

According to a further aspect of at least one embodiment of the invention the anonymized data record is configured to be used as input data by the remote application associated with the processing plug-in. This aspect has the advantage that the anonymized data record can be processed by the remote application associated with the processing plug-in without further preprocessing.

According to a further possible aspect of at least one embodiment of the invention the method furthermore comprises the step of providing the anonymized data record to the remote application associated with the processing plug-in by the cloud data repository.

According to a further possible aspect of at least one embodiment of the invention a first plug-in of the available plug-ins cannot interact directly with a second plug-in of the available plug-ins. In particular, each plug-in of the available plug-ins is executed in a sandbox. In particular, each plug-in of the available plug-ins can only interact with the surrounding via an interface provided by the core module. This possible aspect has the advantage that malfunctions of one plug-in do not affect other plug-ins, which increases the stability of the whole system. Furthermore, malicious plug-ins cannot influence other plug-ins.

According to a further aspect of at least one embodiment of the invention the medical data record comprises a first data item and a second data item, wherein the first data item comprises personal data related to a patient, wherein the anonymized data record comprises the second data item and a data record identifier, and wherein the data record identifier is based on the first data item. The advantage of this aspect of the invention is that only a certain part of the medical data record needs to be anonymized by the local transmission software. This expedites and simplifies the anonymization process. Furthermore, by not altering the second data item standard algorithms for processing the respective data records can be used by the respective remote application. Advantageously the respective remote application is configured to process only the second data item of the anonymized data record.

According to a further possible aspect of at least one embodiment of the invention the local transmission software stores a mapping from the data record identifier to the first data item. In particular, the processing plug-in stores a mapping from the data record identifier to the first data item. The advantage of this possible aspect is that the local transmission software can correlate or associate the anonymized data record (and any data records that are a result of a processing of the anonymized data records by the remote application) with the medical data record or to the first data item. For example, if the remote application associated with the processing plug-in can create a CPU-intensive visualization of the anonymized data record and sends this visualization back to the local transmission software, the visualization can be assigned to the first data item related to personal data of a patient by the local transmission software. In particular a processed medical data record can be created based on the processed anonymized data record. Within the whole process the remote application does have not access to the first data item containing person-related data of a patient.

According to a further aspect of at least one embodiment of the invention the data record identifier is the result of applying an anonymization function of the core module onto the first data item. This aspect of the invention has the advantage that every plug-in of the available plug-ins can use the anonymization functionality of the core module and does not need to implement the anonymization functionality by its own, which then save developing costs. Furthermore having only one anonymization functionality reduces the possible number of critical errors. In particular the anonymization function is a one-way function, in particular the anonymization function is a hash function.

According to a further aspect of at least one embodiment of the invention the data record identifier is based on an anonymization level parameter, and wherein the anonymization level parameter is provided to the anonymization function. This aspect of the invention has the advantage that the available plug-ins can use different levels of anonymization and still use the anonymization functionality of the core module. Different levels of anonymization are needed for different remote applications (e.g. the age or the sex of the patient can be relevant for a certain remote application, so only the name of the patient may be removed or anonymized). It is also thinkable that the level of anonymization used does depend on the medical institution the local transmission software is executed in or the local transmission unit is located in, or on the country the medical institution is located in.

According to a further aspect of at least one embodiment of the invention the processing plug-in is configured to process other data while the uploading is executed by the core module, and the method furthermore comprising the step of notifying by the core module the processing plug-in about the completion of the uploading. A technical term for this behavior is "asynchronous upload". This aspect of the invention has the advantage that the method can be executed faster, because the processing plug-in can e.g. anonymize other data while waiting for the completion of the uploading procedure, or initiate uploads to other cloud data repositories. Furthermore an upload initiated by the processing plug-in does not block interactions between other plug-ins and the core module.

According to another possible aspect of at least one embodiment of the invention the procession plug-in is configured to not process other data until the step of uploading has been completed by the core module. A technical term for this behavior is "synchronous upload". This possible aspect of the invention has the advantage that the development of the plug-ins is easier and cheaper, because a synchronous upload does not have side effects on other parts of the processing plug-in.

According to a further aspect of at least one embodiment of the invention the method furthermore comprises the step of notifying the remote application associated with the processing plug-in about the completion of the uploading of the anonymized data record by sending a notification message from the core module to the remote application associated with the processing plug-in. In particular the notification message can comprise an identifier of the anonymized data record, a hyperlink to the anonymized data record, a hash of the anonymized data record, and/or a timestamp. The advantage of this aspect of the invention is that by this message the remote application can instantaneously start the processing of the anonymized data record, without regularly checking the cloud data repository. This implies an expedited processing of the anonymized data record.

According to a further possible aspect of at least one embodiment of the invention the method furthermore comprises the step of receiving a plug-in installation file by the core module, wherein the plug-in installation file comprises an installable plug-in and a configuration file, and the step of installing the installable plug-in as an additional available plugin based on the configuration file by the core module. In particular the plug-in installation file can be downloaded from a public plug-in repository; alternatively the plug-in installation file can be send to the local transmission software and/or to the local transmission unit manually or by another program. This aspect of the invention has the advantage that set of available plug-ins can be extended by other plug-ins, e.g. if new remote applications are released and/or other local data storages and/or other data formats should be processed by the local transmission software.

According to a further possible aspect of at least one embodiment of the invention the method furthermore comprises the step of deinstalling a plug-in from the step of available plug-ins. Another term for deinstalling is removing. This possible aspect has the advantage that obsolete plug-ins can be removed, so that the memory consumption of the local transmission software decreases and the local transmission software becomes less vulnerable for malicious attacks. In particular together with the previous aspect of the invention a mechanism for uploading one of the available plug-ins can be provided.

According to a further aspect of at least one embodiment of the invention the method comprises the step of determining a resource parameter of a local transmission unit hosting the local transmission software, wherein the resource parameter is based on the memory usage and/or the processor usage of the local transmission unit; the step of initializing a first plug-in of the available plug-ins if the resource parameter is below a lower resource threshold; and the step of terminating a second plug-in of the available plug-ins if the resource parameter is above an upper resource threshold. In particular, the step of initializing a first plug-in is an optional step. In particular the resource parameter is based on the memory usage and/or the processor usage of one of the available plug-ins running within the local transmission unit. In particular the upper resource threshold is higher than the lower resource threshold. This aspect of the invention has the advantage that the number of running plug-ins can be controlled based on the resource parameter, so that there is no blocking overload of the system, and so that there are as much plug-ins as possible running to prevent that a plug-in has to be started prior to receiving a medical data record. If the resource parameter is based on the memory usage and/or the processor usage of one of the available plug-ins running within the local transmission unit, furthermore the one of the available plug-ins can be stopped and/or restarted if it exceeds the upper resource limit in order to ensure that a broken plug-in does not influence the cloud transmission software or the cloud transmission unit, in particular that a broken plug-in does not block the cloud transmission software or the cloud transmission unit.

According to a further aspect of at least one embodiment of the invention the method comprises the step of receiving an action message from the remote application by a cloud transmission software, wherein the action message comprises a plug-in identifier; the step of transmitting the action message from the cloud transmission software through the core module to a receiving plug-in of the available plug-ins, wherein the receiving plug-in is selected by the core module based on the plug-in identifier; and the step of processing the action message by the receiving plug-in. In particular the receiving plug-in can be identical with the processing plug-in. This aspect of the invention has the advantage that the remote application can interact with the receiving plug-in, e.g. to trigger a search for new data, to alter a configuration of the receiving plug-in (e.g. the anonymization level used) or to initialize and/or terminate the receiving plug-in.

According to a further aspect of at least one embodiment of the invention the method for uploading a data record to a cloud data repository furthermore comprises the step of generating a processed data record based on the anonymized data record by the remote application associated with the processing plug-in; the step of storing the processed data record in the cloud data repository by the remote application associated with the processing plug-in; the step of notifying the local transmission software about the storing of the processed data record by sending a message from the remote application associated with the processing plug-in to the local transmission software; the step of downloading the processed data record from the cloud data repository by the processing plug-in; and the step of storing the processed data record within a local data repository by the processing plug-in. This aspect of the invention has the advantage that remote application can be used to process data records in a flexible and extensible way, so that additional resources can be used flexible without changing the hardware configuration of the local hospital site.

According to a further possible aspect of at least one embodiment of the invention the method furthermore comprises the step of sending a status inquiry message from the core module to one plug-in of the available plug-ins; and the step of sending a status reply message from the the one plug-in of the available plug-ins to the core module, wherein the status reply message comprises a parameter describing the status of the the one plug-in of the available plugins. In particular the the one plug-in can be identical with the processing plug-in. In particular, the the one plug-in of the available plug-ins can be identical with the receiving plug-in. This aspect of the invention has the advantage of providing a mechanism for checking the available plug-ins, and for e.g. notifying a user about a malfunction of the the one plug-in.

At least one embodiment of the invention furthermore relates to a method for generating an anonymized data record, comprising:

receiving a medical data record by a local transmission software, wherein the local transmission software comprises a core module and available plug-ins, wherein each available plug-in of the available plug-ins is associated with a remote application; and generating an anonymized data record based on the medical data record by a processing plug-in, wherein the processing plug-in is one of the available plug-ins, and wherein the anonymized data record is configured to be input data for the remote application associated with the processing plug-in.

In particular the method for generating an anonymized data record of at least one embodiment is a computer-implemented method. The step of receiving the medical data record of the method for generating a anonymize data record can comprise the advantageous embodiments and features of the step of receiving the medical data record of the method for uploading a data record. The step of generating an anonymized data record of the method for generating a medical data record can comprise the advantageous embodiments and features of the step of generating an anonymized data record of the method for uploading a data record.

The method for generating an anonymized data record of at least one embodiment can furthermore comprise the following:

Receiving a plug-in installation file by the core module, wherein the plug-in installation file comprises an installable plug-in and a configuration file, and Installing the installable plug-in as an additional available plugin based on the configuration file.

The method for generating an anonymized data record can furthermore comprise the following:

Determining a resource parameter of a local transmission unit hosting the local transmission software, wherein the resource parameter is based on the memory usage and/or the processor usage of the local transmission unit, Initializing a first plug-in of the available plug-ins, if the resource parameter is below a lower resource threshold, and Terminating a second plug-in of the available plug-ins, if the resource parameter is above an upper resource threshold, wherein the upper resource threshold is higher than the lower resource threshold.

The method for generating an anonymized data record can furthermore comprise the following:

Receiving (REC-3) an action message from the remote application by a cloud transmission software, wherein the action message comprises a plug-in identifier, Transmitting (TRM) the action message from the cloud transmission software through the core module to a receiving plug-in of the available plug-ins, wherein the receiving plug-in is selected by the core module based on the plug-in identifier, and Processing (PROC) the action message by the receiving plug-in.

The invention of at least one embodiment furthermore relates to a local transmission unit configured to host a local transmission software for uploading a data record to a cloud data repository, wherein the local transmission software comprises a core module and available plug-ins, wherein each available plug-in of the available plug-ins is associated with a remote application;

wherein the local transmission unit is configured to receive a medical data record by a local transmission software;

wherein the local transmission unit is configured to generate an anonymized data record based on the medical data record by a processing plug-in, wherein the processing plug-in is one of the available plug-ins;

wherein the local transmission unit is configured to upload the anonymized data record to a cloud data repository by the core module, wherein the anonymized data record in the cloud data repository is accessible by the remote application associated with the processing plug-in.

In particular the local transmission unit can be configured to execute the method for uploading a data record to a cloud data storage or the method for generating an anonymized data record according to at least one embodiment of the invention and its aspects. The local transmission unit is configured to execute the method for uploading a data record to a cloud data storage or the method for generating an anonymized data record and its aspects by a calculation unit and a memory unit of the local transmission unit being configured to execute the respective method steps.

The local transmission unit can comprise hardware and/or software. The hardware can be, for example, a processor system, a memory system and combinations thereof. The hardware can be configurable by the software and/or be operable by the software.

At least one embodiment of the invention relates in one aspect to a computer program product comprising a local transmission software, the local transmission software being loadable into a memory unit of a local transmission unit, including program code sections to make the local transmission unit execute the method for uploading a data record into a cloud data repository or the method for generating an anonymized data record according to an aspect of at least one embodiment of the invention when the local transmission software is executed in the local transmission unit. In particular, the local transmission software is a computer program product.

At least one embodiment of the invention relates in one aspect to a computer-readable medium, on which program code sections of a local transmission software are saved, the program code sections being loadable into and/or executable in a local transmission unit to make the providing system execute the method for uploading a data record into a cloud data repository or the method for generating an anonymized data record according to an aspect of at least one embodiment of the invention when the program code sections are executed in the local transmission unit.

The realization of at least one embodiment of the invention by a computer program product and/or a computer-readable medium has the advantage that already existing local transmission units can be easily adopted by software updates in order to work as proposed by at least one embodiment of the invention.

The computer program product can be, for example, a computer program or comprise another element apart from the computer program. In particular, the computer program product can be, for example, the local transmission software or comprise another element apart from the local transmission software. This other element can be hardware, for example a memory device, on which the computer program is stored, a hardware key for using the computer program and the like, and/or software, for example a documentation or a software key for using the computer program, or an installation routine.

At least one embodiment of the invention furthermore relates in one aspect to a method for installing an installable plug-in within the the local transmission software or within the the local transmission unit, comprising:

receiving a plug-in installation file by the core module of a local transmission software, wherein the plug-in installation file comprises an installable plug-in and a configuration file; and installing the installable plug-in as an additional available plugin within a local transmission software or within a local transmission unit based on the configuration file.

In particular the method for installing an installable plug-in within the the local transmission software or within the the local transmission unit is a computer-implemented method.

At least one embodiment of the invention furthermore relates in one aspect to a method for initializing or terminating a plug-in within the the local transmission software or within the the local transmission unit, comprising:

determining a resource parameter of a local transmission unit hosting the local transmission software, wherein the resource parameter is based on the memory usage and/or the processor usage of the local transmission unit, initializing a first plug-in of the available plug-ins, if the resource parameter is below a lower resource threshold, and terminating a second plug-in of the available plug-ins, if the resource parameter is above an upper resource threshold, wherein the upper resource threshold is higher than the lower resource threshold.

In particular the method for initializing or terminating a plug-in within the the local transmission software or within the the local transmission unit is a computer-implemented method.

At least one embodiment of the invention furthermore relates in one aspect to a method for processing an action message within the the local transmission software or within the the local transmission unit, comprising:

receiving an action message from the remote application by a cloud transmission software, wherein the action message comprises a plug-in identifier, transmitting the action message from the cloud transmission software through the core module to a receiving plug-in of the available plug-ins, wherein the receiving plug-in is selected by the core module based on the plug-in identifier, and processing the action message by the receiving plug-in.

In particular the method for processing an action message within the the local transmission software or within the the local transmission unit is a computer-implemented method.

At least one embodiment of the invention furthermore relates in one aspect to a method for storing a processed data record within a local data repository, comprising:

generating a processed data record based on an anonymized data record by a remote application associated with a processing plug-in, wherein the anonymized data record is stored in a cloud data repository, storing the processed data record in the cloud data repository by the remote application associated with the processing plug-in, notifying a local transmission software about the storing of the processed data record by sending a message from the remote application associated with the processing plug-in to the local transmission software, downloading the processed data record from the cloud data repository by the processing plug-in, and storing the processed data record within a local data repository by the processing plug-in.

In particular, the local transmission unit and/or the local transmission software comprise the local data repository. In particular the local transmission software is notified about the storing of the processed data record by sending a message from the remote application associated with the processing plug-in to a core module of the local transmission software, and by forwarding the message from the core module to the processing plug-in. In particular, the local data repository is associated with the processing plug-in.

In particular the local transmission unit can be configured to execute the method for generating an anonymized data record according to an aspect of at least one embodiment of the invention, the method for installing an installable plug-in within the the local transmission software or within the the local transmission unit, the method for initializing or terminating a plug-in within the the local transmission software or within the the local transmission unit, the method for processing an action message within the the local transmission software or within the the local transmission unit, or the method for storing a processed data record within a local data repository. The local transmission unit is configured to execute the method and its aspects by a calculation unit and a memory unit of the local transmission unit being configured to execute the respective method steps.

At least one embodiment of the invention relates in one aspect to a computer program product comprising a local transmission software, the local transmission software being loadable into a memory unit of a local transmission unit, including program code sections to make the local transmission unit execute the method for generating an anonymized data record according to an aspect of at least one embodiment of the invention, the method for installing an installable plug-in within the the local transmission software or within the the local transmission unit, the method for initializing or terminating a plug-in within the the local transmission software or within the the local transmission unit, the method for processing an action message within the the local transmission software or within the the local transmission unit, or the method for storing a processed data record within a local data repository, when the local transmission software is executed in the local transmission unit. In particular, the local transmission software is a computer program.

At least one embodiment of the invention relates in one aspect to a computer-readable medium, on which program code sections of a local transmission software are saved, the program code sections being loadable into and/or executable in a local transmission unit to make the providing system execute, the method for generating an anonymized data record according to an aspect of at least one embodiment of the invention, the method for installing an installable plug-in within the the local transmission software or within the the local transmission unit, the method for initializing or terminating a plug-in within the the local transmission software or within the the local transmission unit, the method for processing an action message within the the local transmission software or within the the local transmission unit, or the method for storing a processed data record within a local data repository, when the program code sections are executed in the local transmission unit.

A medical data record is a data record comprising at least one result of a medical examination of a patient, and at least one person-related data item of the patient. An anonymized data record generated based on a medical data record is a data record comprising the at least one result of a medical examination of a patient of the medical data record. In particular, the anonymized data record comprises less person-related data items of the medical data record than the medical data record; in particular the anonymized data record comprises no person-related data item of the medical data record. It is to be understood that an anonymized data record does not comprise a person-related data item, if the anonymized data record does comprise an encrypted and/or encoded version of the the person-related data item, wherein the the person-related data item cannot be reconstructed from the encrypted and/or encoded version of the the person-related data item. In particular, the anonymized data record does not comprise a person-related data item if the the anonymized data record comprises a hash values of the the person-related data item.

The term cloud computing describes the usage of shared processing and storage resources, wherein these shared resources are connected among themselves and to the external user via the internet or an intranet, and wherein these shared resources are in general locally or geographically separated from the user. In particular, the shared processing and storage resources need not to be arranged in a common location, they can be distributed to different locations. A cloud describes a group of shared processing and storage resources, e.g. provided by a third party (e.g. Amazon Web Services or Microsoft Azure cloud). The term cloud storage is used as an alternative term for the shared storage resources. A cloud can also comprise an interface for accessing the shared resources (e.g. to start or stop a calculation job, or for uploading or downloading data to the cloud storage), in particular an API (acronym for "application programming interface"), in particular a Web API. A cloud can also comprise software components using the shared processing and storage resources, e.g. web applications running on a server, which can be used within a browser of an user.

An application programming interface (short term "API") is a set of functions and/or methods for interaction between at least two software components. In general, a first software component provides an API that can be used by a second software component. Therefore the second component can call the functions and/or methods of the API, providing (possibly empty) input data for the functions and/or methods and receive (possibly empty) output data from the functions and/or methods. A Web API is an API provided by a web server or a web browser, in particular a Web API is a web service implementing "Representational state transfer" (an acronym is "REST", therefore another term is RESTful web service) or implementing the "Simple Object Access Protocol" (an acronym is "SOAP").

A remote application is software or a computer program, in particular an on-premises application, a virtual machine application and/or a cloud application. In particular, the remote application is not executed by the local transmission unit. In particular, the core module and the available plug-ins are software or computer programs; in particular both are an on-premises application.

An on-premises application is software or a computer program which is executable locally on a computation device of the person or institution using the on-premise application, in particular within an operating system of the computation device. The local application comprises program code sections, which are executed by a calculation unit of the computation device and which optionally store intermediate results within a memory unit of the computation device.

A virtual machine application is software or a computer program which is executable in an emulation of a first computation device, in particular within a virtual machine hosted by a second computation device. In general the virtual machine provides an operating system hosting the virtual machine application. In particular the virtual machine is an on-premises application. The second computation device can be local hardware of the user; in this case the interaction with the virtual machine is done by interacting with the second computing device. Alternatively the second computation device can be a non-local server (within the cloud); in this case the interaction with the virtual machine is done by a software program on the hardware of the user, in particular a web browser.

A cloud application is software or a computer program physically running on a server or within a cloud, i.e. consuming processing and/or storage resources of the server or of the cloud. The interaction between the user and the cloud application is usually done by a web browser executed on user hardware. Other terms for cloud application are "software as a service" or "on-demand software".

Advantageously the local transmission software, the core module and the available plug-ins are on-premises software executed on the local transmission unit. Advantageously the cloud transmission software is a cloud application.

The term cloud storage denotes a storage solution for data and/or files within the cloud, in particular within the shared memory resources. The underlying physical storage can be distributed to multiple physical units and/or locations. In particular, the cloud data repository comprises cloud storage and an API to access this cloud storage.

A plug-in is associated with a remote application (or vice-versa), if an anonymized data record generated by the plug-in is configured to be used as input data for the remote application. In particular a plug-in is associated with a remote application (or vice-versa), if the format of an anonymized data record generated by the plug-in can be processed by the remote application.

The term available plug-ins describes all plug-ins that can be used within the local transmission software and/or on the local transmission unit. In particular, the term available plug-in describes all plug-ins that are actively running within the local transmission software and/or on the local transmission unit. In other words, if a plug-in is a computer program, a plug-in is available if the plug-in is running as process within the local transmission unit (or if the plug-in is running in a separate Application Domain, e.g. defined in the Microsoft .NET framework). Alternatively, the term available plug-in can also describe all plug-ins that are installed within the local transmission software and/or on the local transmission unit. In other words, the term available plug-in can describe all running and non-running plug-ins within the local transmission software and/or on the local transmission unit.

FIG. 1 shows an embodiment of the local transmission software 10. The local transmission software comprises a core module 11 and several available plugins 12.1, 12.2, 12.P. Advantageously, each of the available plug-ins 12.1, 12.2, 12.P can store data in a plug-in-specific storage 13.1, 13.2, 13.P within the local transmission software. Each of the available plugins 12.1, 12.2, 12.P receives data from a local data repository 14.1, 14.2, 14.P. The local transmission software 10 is installed on a local transmission unit 20 within a single medical institution, e.g. a hospital or a group of hospitals.

The local data repositories 14.1, 14.2, 14.P are located in the same single medical institution as the local transmission unit 20, they contain medical data records MDR. In general the local data repositories 14.1, 14.2, 14.P cannot be accessed from outside the single medical institution to ensure data privacy of the medical data records MDR. Examples for local data repositories 14.1, 14.2, 14.P are PACS (acronym for "Picture Archiving and Communication System"), HIS (acronym for "Hospital Information System"), LIS (acronym for "Laboratory Information System") and RIS (acronym for "Radiology Information System"). There can be a one-to-one correspondence between local data repositories 14.1, 14.2, 14.P and available plugins 12.1, 12.2, 12.P, alternatively an arbitrary number of local data repositories 14.1, 14.2, 14.P can be associated with one of the available plugins 12.1, 12.2, 12.P and/or an arbitrary number of available plugins 12.1, 12.2, 12.P can be associated with one of the local data repositories 14.1, 14.2, 14.P.

In the displayed embodiment the local transmission software 10, specifically the core module 11, is in communication with a cloud transmission software 15. The cloud transmission software 15 is in this embodiment a cloud application. The cloud transmission software 15 receives anonymized data records ADR from the local transmission software 10 and stores the anonymized data records ADR in cloud data repository 16. The cloud data repository 16 is often denoted as blob storage.

Furthermore there are several remote applications 17.1, 17.2, 17.P located in the cloud. The remote applications 17.1, 17.2, 17.P can access the cloud data repository 16; in particular the remote applications 17.1, 17.2, 17.P can access the anonymized data records ADR within the cloud data repository 16. Each of the available plugins 12.1, 12.2, 12.P is associated with a remote application 17.1, 17.2, 17.P, in other words each of the available plugins 12.1, 12.2, 12.P prepares anonymized data records ADR for one of the remote applications 17.1, 17.2, 17.P. In this embodiment, the plug-in 12.1 is associated with the remote application 17.1, the plug-in 12.2 is associated with the remote application 17.2, and the plug-in 12.P is associated with the remote application 17.P.

Advantageously the cloud data repository 16 comprises sub-repositories 16.1, 16.2, 16.P associated with the remote applications 17.1, 17.2, 17.P, so that one of the remote applications 17.1, 17.2, 17.P can only access the data within one of the sub-repositories 16.1, 16.2, 16.P, if the one of the remote applications 17.1, 17.2, 17.P is associated with the one of the sub-repositories 16.1, 16.2, 16.P. There can be a one-to-one correspondence between remote applications 17.1, 17.2, 17.P and sub-repositories 16.1, 16.2, 16.P, alternatively an arbitrary number of remote applications 17.1, 17.2, 17.P can be associated with one of the sub-repositories 16.1, 16.2, 16.P and/or an arbitrary number of sub-repositories 16.1, 16.2, 16.P can be associated with one of the remote applications 17.1, 17.2, 17.P. The advantage of this alternative is an increased data protection compared to a case where every one of the remote applications 17.1, 17.2, 17.P can access all the data from the cloud data repository 16.

In this embodiment there is a one-to-one correspondence between the available plug-ins 12.1, 12.2, 12.P and the remote applications 17.1, 17.2, 17.P. Alternatively it is also possible that an available plug-in 12.1, 12.2, 12.P is associated with several remote applications 17.1, 17.2, 17.P. Alternatively it is also possible that one remote application 17.1, 17.2, 17.P is associated with several available plug-ins 12.1, 12.2, 12.P.

In this embodiment, a remote application 17.1, 17.2, 17.P can communicate with its associated plug-in 12.1, 12.2, 12.P by sending messages through the cloud transmission software 15 and the core module 11 to its associated plug-in 12.1, 12.2, 12.P. This communication channel is optional, which is indicated by a dotted line, it can be used e.g. for triggering a data retrieval by the associated plug-in 12.1, 12.2, 12.P, or for sending data to the associated plug-in 12.1, 12.2, 12.P.

In this embodiment, in particular the core module 11 and the available plug-ins 12.1, 12.2, 12.P communicate using API calls. It is also thinkable that they communicate using reserved storage space within the memory unit 23 of a local transmission unit 20, by creating, modifying and deleting files within the reserved storage space, wherein the reserved storage space can be accessed by both the core module 11 and at least one of the available plug-ins 12.1, 12.2, 12.P. In particular, a medical data record MDR or an anonymized data record ADR can be transferred from the processing plug-in 12.P to the core module 11 by storing the anonymized data record ADR within the reserved storage space by the processing plug-in 12.P, and by accessing the anonymized data record ADR within the reserved storage space by the core module 11.

In this embodiment the core module 11 provides the following methods and/or functions by an API for the available plug-ins 12.1, 12.2, 12.P:

Upload_Sync(data_record): Synchronous function which is used to upload UPL an anonymized data record ADR to the cloud data repository 16. This function is a blocking function. The function returns a hyperlink which can be used for accessing the anonymized data record ADR within the cloud data repository 16.

Upload_Async(data_record): Asynchronous function which is used to upload UPL an anonymized data record ADR to the cloud data repository 16. This function is a non-blocking function. The function returns a hyperlink which can be used for accessing the anonymized data record ADR within the cloud data repository 16.

Anonymize(data_item, level): Function to anonymize a given data item using a given anonymization level. The function returns the anonymized data item.

In this embodiment the plug-ins 12.1, 12.2, 12.P provide the following methods and/or functions by an API for interaction with the core module:

Start(command_message): Function which is used to load the plug-in 12.1, 12.2, 12.P to the local transmission software 10. Function accepts an optional command message data as input and shall return a Boolean to indicate the status of the operation.

Stop(command_message): Function which is used to notify the plug-in 12.1, 12.2, 12.P that it should stop its activity. Function accepts an optional command message data as input and shall return a Boolean to indicate the status of the operation.

Restart(command_message): Function which is used to notify the plug-in 12.1, 12.2, 12.P that it should stop and restart its activity. Function accepts an optional command message data as input and shall return a Boolean to indicate the status of the operation.

Message(command_message): Function which is used to dynamically pass messages from core module 11 to plugins

12.1, 12.2, 12.P. Function accepts a mandatory message data as input and shall return a Boolean to indicate the status of the operation.

Ping( ): Shall return true if the plug-in 12.1, 12.2, 12.P is running and successfully loaded by the core module 11.

IsOperable( ): Shall return true if the plug-in 12.1, 12.2, 12.P is able to make use of the core module 11 provided services, and do it's expected functionality without any infrastructure problems.

Figure 2:
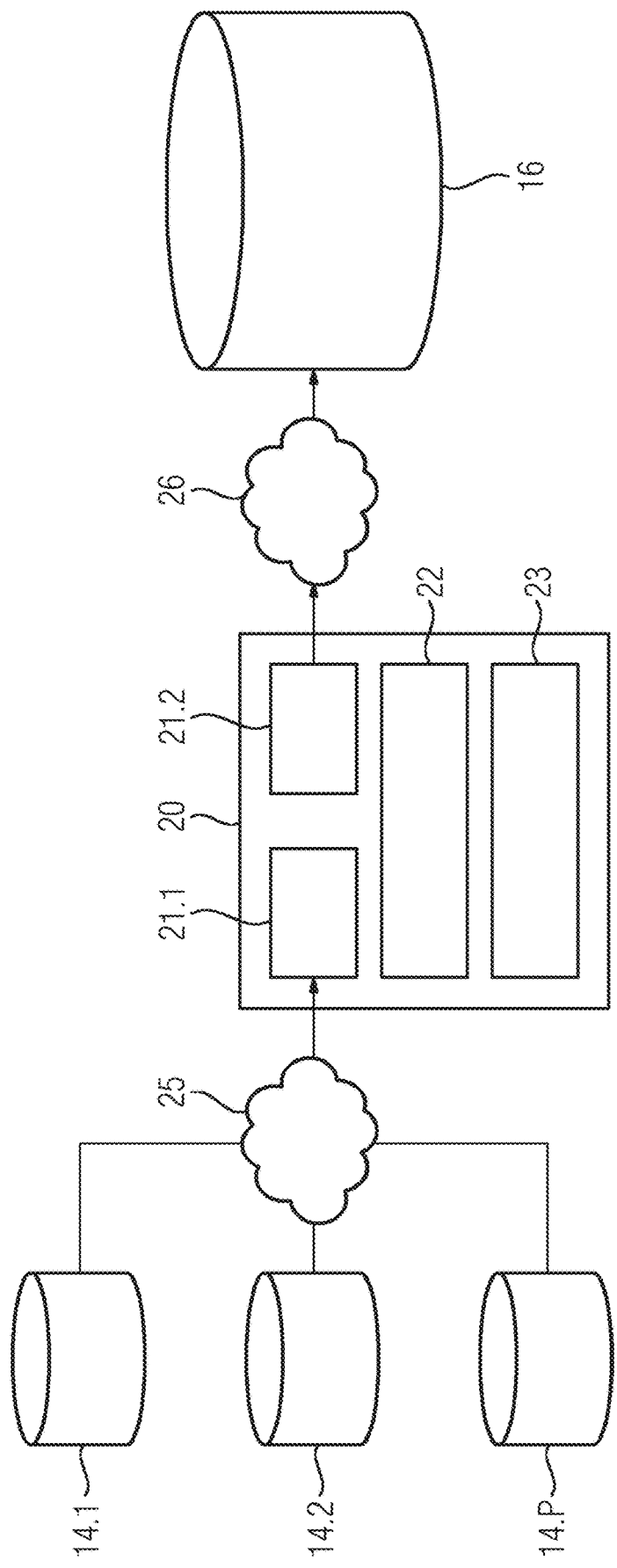
FIG. 2 shows an embodiment of the local transmission unit.

FIG. 2 shows an embodiment of a local transmission unit comprising an input interface 21.1, an output interface 21.2, and calculation unit 22 and a memory unit 23. The local transmission unit can be a (personal) computer, a workstation, a virtual machine running on host hardware, a microcontroller, or an integrated circuit. As an alternative, the local transmission unit 20 can be a real or a virtual group of computers (the technical term for a real group of computers is "cluster", the technical term for a virtual group of computers is "cloud").

An input interface 21.1 and an output interface 21.2 can be embodies as a hardware interface or as a software interface (e.g. PCI-Bus, USB or Firewire). In general, a calculation unit 22 can comprise hardware elements and software elements, for example a microprocessor, a CPU (acronym for "central processing unit"), a GPU (acronym for "graphical processing unit") or a field programmable gate array. The calculation unit 22 can be configured for multithreading, i.e. the calculation unit 22 can host different calculation processes at the same time, executing the either in parallel or switching between active and passive calculation processes. A memory unit 23 can be e.g. non-permanent main memory (e.g. random access memory) or permanent mass storage (e.g. hard disk, USB stick, SD card, solid state disk).

In this embodiment the local transmission unit 20 is connected to local data storages 14.1, 14.2, 14.P by a first network 25. The first network 25 can be realized as a LAN (acronym for "local area network"), in particular a WiFi network, or any other local connection, e.g. via Bluetooth or USB (acronym for "universal serial bus"). The first network 25 can alternatively also be realized as a VPN (acronym for "virtual private network"). Alternatively the local transmission unit 20 can also be identical with one of the local data repositories 14.1, 14.2, 14.P, e.g. if the local transmission software 10 is installed on e.g. the PACS or the HIS.

In this embodiment the local transmission unit 20 is connected to the cloud data repository 16 by a second network 26. Usually at least a part of the second network 26 is the internet. There can be other applications and services mediating the connection between the local transmission unit and the cloud data repository 16, e.g. a cloud transmission software 15. These other applications and services can influence the data transmission between the local transmission unit 20 and the cloud data repository 16. The first network 25 and the second network 26 may be identical.

Figure 3:
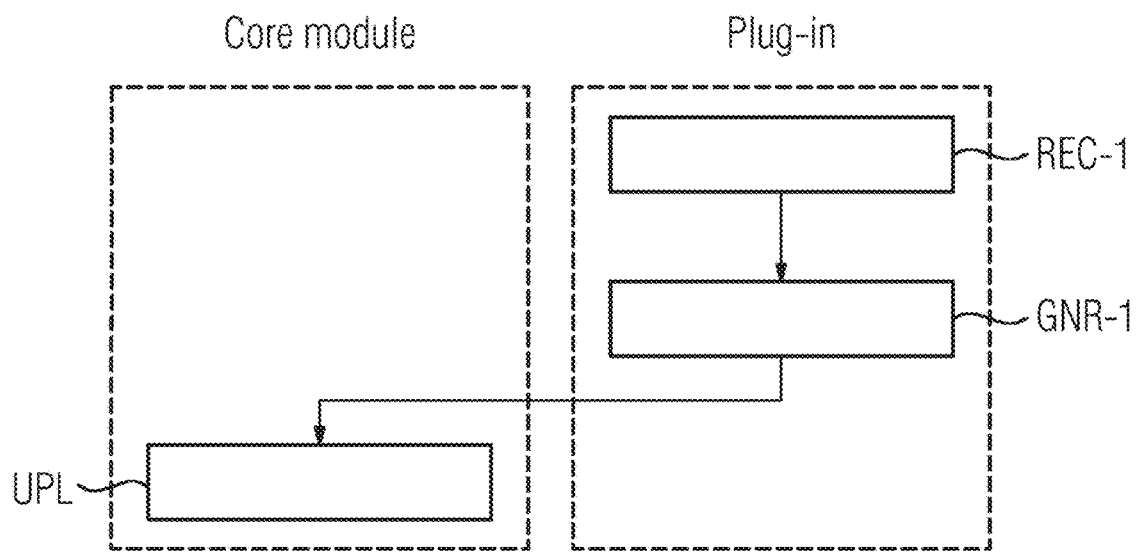
FIG. 3 shows a flowchart of a first embodiment of the method for uploading a data record to a cloud data repository.

FIG. 3 shows a first embodiment of the method for uploading a data record into a cloud data repository 16. The first step of this first embodiment is receiving REC-1 a medical data record MDR by a local transmission software 10, wherein the local transmission software 10 comprises a core module 11 and available plug-ins 12.1, 12.2, 12.P, wherein each available plug-in 12.1, 12.2, 12.P of the available plug-ins 12.1, 12.2, 12.P is associated with a remote application 17.1, 17.2, 17.P. In particular, the step of receiving REC-1 is performed by the input interface 21.1.

In this first embodiment the medical data record MDR is transferred from a local data repository 14.1, 14.2, 14.P directly to the processing plug-in 12.P, so within the step of receiving REC-1 the medical data record MDR is not processed by the core module 11. This is realized by the processing plug-in 12.P checking for new medical data records MDR in a certain time interval, and initiating a transfer of the new medical data record MDR from the local data repository 14.1, 14.2, 14.P to the processing plug-in 12.P. Herein a medical data record MDR is considered as a new if the medical data record MDR was not present during the previous checking by the processing plug-in 12.P. This can be achieved by either inspecting the creation time and/or the storage time of the medical data records, or by comparing all medical data records MDR of the local data repository with a list of all medical data records MDR received by the processing plug-in 12.P, e.g. by using hash values. Alternatively the local data repository 14.1, 14.2, 14.P can be configured to send each medical data record MDR directly to the associated processing plug-in 12.P after it has been stored within the local data repository 14.1, 14.2, 14.P.

In this first embodiment there is a one-to-one correspondence between the available plug-ins 12.1, 12.2, 12.P and the remote applications 17.1, 17.2, 17.P, as well as a one-to-one correspondence between the available plug-ins 12.1, 12.2, 12.P and the local data repositories 14.1, 14.2, 14.P.

The second step of this first embodiment is generating GNR-1 an anonymized data record ADR based on the medical data record MDR by a processing plug-in 12.P, wherein the processing plug-in 12.P is one of the available plug-ins 12.1, 12.2, 12.P. In particular, the step of receiving GNR-1 is performed by the processing plug-in 12.P executed on the calculation unit 22.

In this first embodiment, the medical data record MDR comprises a first data item D.1 and a second data item D.2, wherein the first data item D.1 comprises personal data related to a patient, wherein the anonymized data records ADR comprises the second data item D.2 and a data record identifier AD, wherein the data record identifier AD is based on the first data item D.1. For example, if the medical data record MDR is an imaging study, the first data item D.1 may comprise the name, the age and the sex of the patient subject to the imaging study, and the second data item D.2 may comprise the actual images of the imaging study. As another example, if the medical data record MDR is a laboratory report, the first data item D.1 may comprise the name and the age of the patient subject to the laboratory report, and the second data item D.2 may comprise the actual laboratory data. So the first data item D.1 can also be denoted as person-related data, and the second data item D.2 can also be denoted as medical result data.

In this first embodiment, the data record identifier AD is the hash of the first data item D.1 calculated with the SHA-1 hash algorithm (acronym for "Secure Hash Algorithm"). Alternatively the data record identifier AD can also be the hash of the whole medical data record MDR, or any other hash algorithm can be used, e.g. MD5 (acronym for "Message-Digest Algorithm 5"), SHA-2 (in particular SHA-224, SHA-256, SHA-384, SHA-512, SHA-512/224, SHA-512/256), SHA-3 (in particular SHA3-224, SHA3-256, SHA3-384, SHA3-512, SHAKE128 and HAKE256), BLAKE, Grøstl, JH or Skein. By using a hash algorithm it is not possible to extract the first data item D.1 from the data record identifier AD, so in particular the remote applications 17.1, 17.2, 17.P cannot access or deduce the first data item D.1. The available plug-ins 12.1, 12.2, 12.P store a mapping between the data record identifier AD and the first data item D.1 within the local plug-in storage 13.1, 13.2, 13.P. By storing this mapping the first data item D.1 can be reassigned to the anonymized data records ADR, but only in the local environment. By this mechanism it is possible to process the anonymized data records ADR using remote applications (e.g. to provide a sophisticated and CPU-intensive rendering), and to map the processed data to the personal data of the patient in the local hospital environment.

The third step of this first embodiment is uploading UPL the anonymized data records ADR to a cloud data repository 16 by the core module 11, wherein the anonymized data record ADR in the cloud data repository 16 is accessible by the remote application 17.P associated with the processing plug-in 12.P. In particular, the step of uploading UPL is performed by the core module executed on the calculation unit 22 and by the output interface 21.1.

In this first embodiment, the data upload to the cloud data repository 16 is managed by a cloud transmission software 15, wherein the cloud transmission software 15 provides an API for uploading and downloading (other words are "storing" and "retrieving") of data records to or from the cloud data repository 16. In particular, the cloud transmissions service 15 can be an FTP-server (acronym for "file transfer protocol") or an SFTP-server (acronym for "secure file transfer protocol", an alternative name is "SSH file transfer protocol"), which can handle upload and download requests for data files with arbitrary format. The remote application 17.P associated with the processing plug-in 12.P can then access either the cloud data repository 16 directly or by interacting with the cloud transmission software 15 as FTP-server or SFTP server. Alternatively the API can also be a proprietary API specifically designed for the invention, and not related to other known APIs for data upload.

In the displayed first embodiment both the core module 11 and the available plug-ins 12.1, 12.2, 12.P are processes running within an operating system of a local transmission unit 20, using inter-process communication (an acronym is "IPC") for exchanging messages and data. The processes run in particular on the calculation unit 22 of the local transmission unit 20. To each process a unique process identifier is assigned, preferable an integer number. The operation system can start, stop, pause and continue processes; the different processes can run in parallel or quasi-parallel (by starting or stopping processes at a high frequency, in particular with a frequency above 10 Hz). Examples for operating systems are Microsoft Windows, e.g. in the Versions 7, 8 or 10, or an operating system based on the Linux Kernel, e.g. Debian or Ubuntu.

To both the core module 11 and each of the plug-ins 12.1, 12.2, 12.P an exclusive memory area is assigned within the memory unit 23, which they can use e.g. for instantiating and storing local variables. Furthermore, both the core module 11 and the plug-ins 12.1, 12.2, 12.P have access to a common memory area, so that they e.g. can access files in a file system.

In general IPC can be a memory-based communication or a message-based communication. Examples for memory-based communication are the usage of shared memory, e.g. located within the memory unit 23 of the local transmission unit 20, or the information exchange using files in a file system (preferable using a lock and unlock mechanism for the single files). Examples for message-based communication are the usage of message queuing, (nameless) pipes, named pipes (an alternative technical term is FIFO pipes) or sockets. In this first embodiment the IPC is done using a message queue, alternatively the other presented methods can be used.

Figure 4:
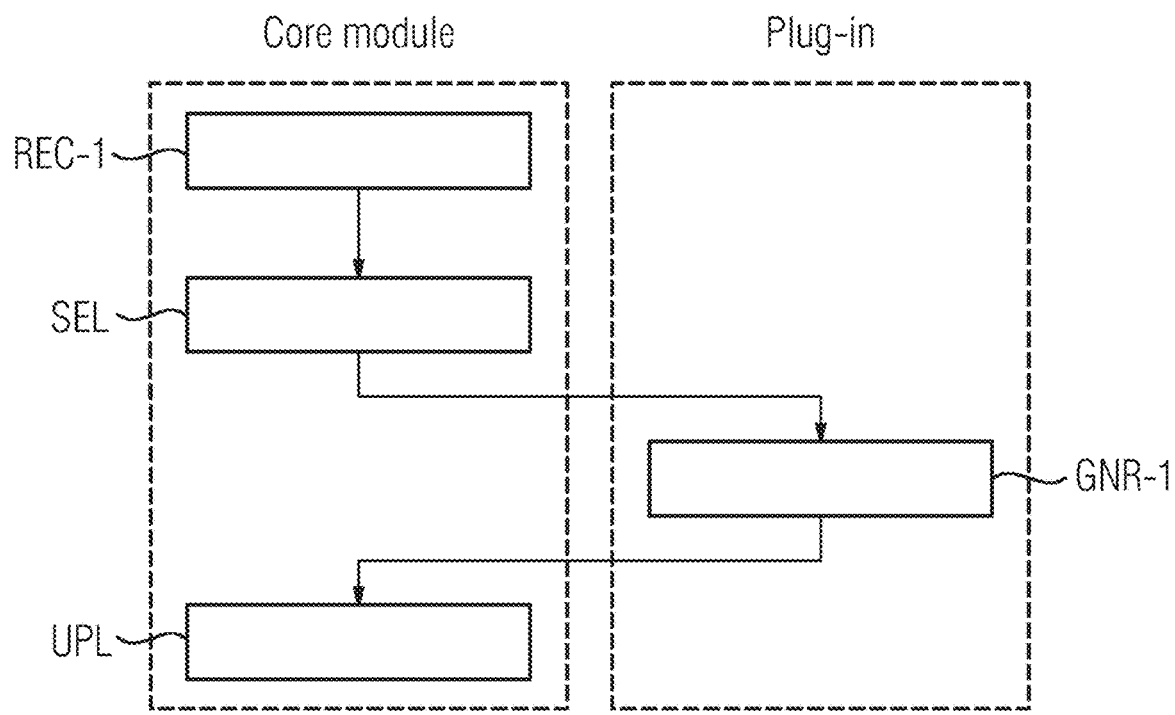
FIG. 4 shows a flowchart of a second embodiment of the method for uploading a data record to a cloud data repository.

FIG. 4 shows a second embodiment of the method for uploading a data record into a cloud data repository 16. In contrast to the first embodiment displayed in FIG. 3, in this second embodiment the medical data record MDR is received REC-1 by the core module 11. This is realized by the local data repositories 14.1, 14.2, 14.P being configured to send every medical data record MDR directly to the core module 11 after the medical data record MDR has been stored in the local data repository 14.1, 14.2, 14.P, or after the medical data record MDR stored within the local data repository 14.1, 14.2, 14.P has been altered. Alternatively the core module 11 can be configured to check for new medical data records MDR within the local data repositories 14.1, 14.2, 14.P in a certain time interval, and initiating a transfer of the new medical data record MDR from the local data repository 14.1, 14.2, 14.P to the core module 11. Herein a medical data record MDR is considered as a new medical data record MDR, if the medical data record MDR was not present during the previous checking by the core module 11. This can be achieved by either inspecting the creation time and/or the storage time of the medical data records MDR, or by comparing all medical data records MDR of the local data repository with a list of all medical data records MDR received by the core module, e.g. by using a hash values.

The second step of the second embodiment displayed in FIG. 4 is selecting SEL the processing plug-in 12.P from the available plug-ins 12.1, 12.2, 12.P by the core module 11 based on the medical data record MDR. In particular, the step of selecting SEL is performed by the core module 11 executed on the calculation unit 22. In this second embodiment the core module 11 determines the data format of the medical data record MDR and selects the processing plug-in 12.P based on the determine data format. For example, if the data format is DICOM, the core module 11 will select a processing plug-in 12.P configured to anonymize and/or process DICOM data. The core module 11 can also take into account other aspects of the medical data record MDR, e.g. the medical apparatus the medical data file was created with, to send the medical data record MDR to a vendor-specific processing plug-in 12.P or to an apparatus-specific processing plug-in 12.P. One can for example imagine that there is an available plug-in 12.1, 12.2, 12.P configured to anonymize medical data records MDR originating from a magnetic resonance tomography apparatus, and another available plugin 12.1, 12.2, 12.P configured to anonymize medical data records MDR originating from a computed tomography apparatus.

The steps of generating GNR-1 an anonymized data records ADR by the processing plug-in 12.P and of uploading UPL the anonymized data records ADR by the core module 11 to a cloud data repository 16 are identical with the second embodiment of the method displayed and explained in FIG. 3.

Figure 5:
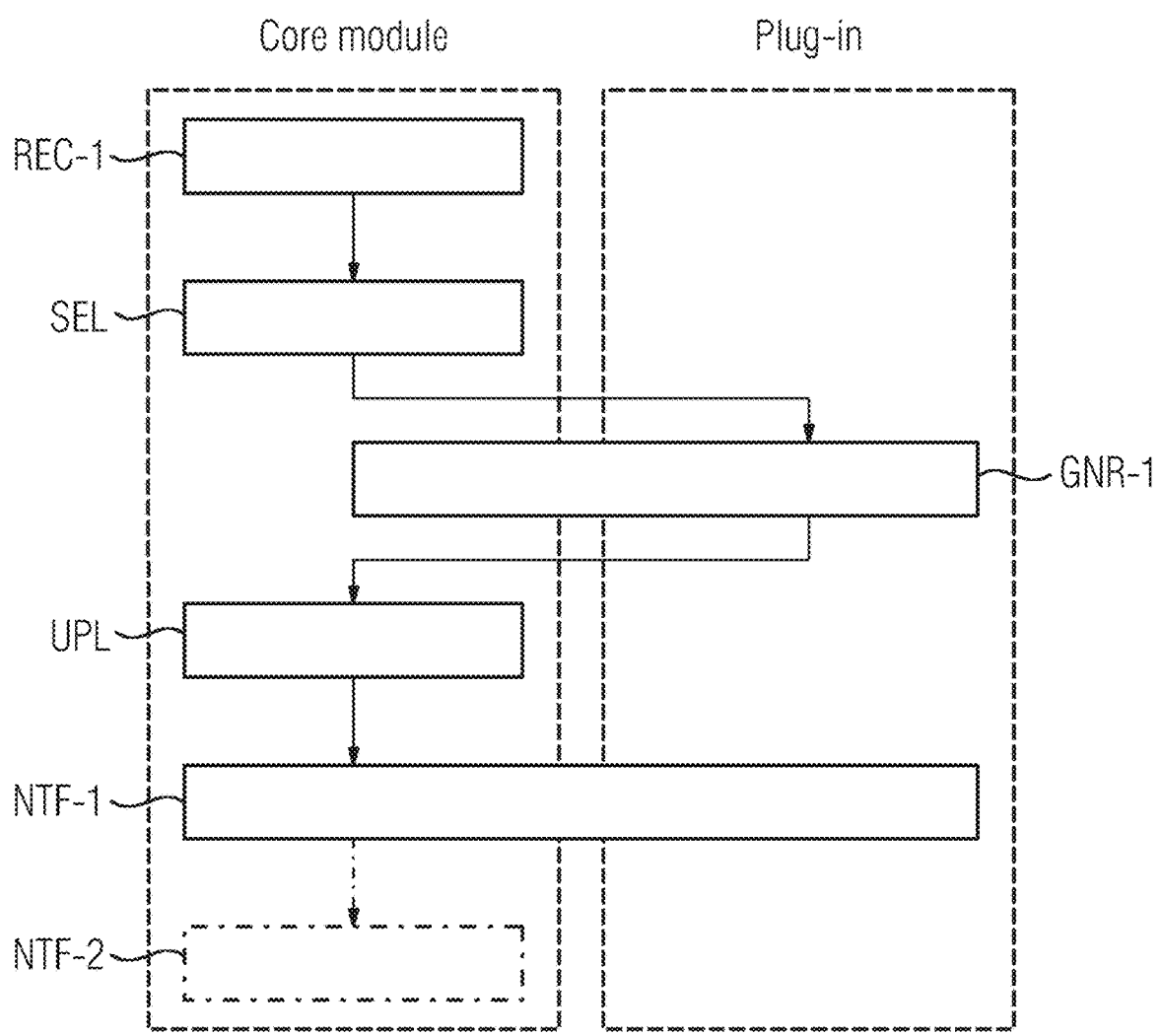
FIG. 5 shows a flowchart of a third embodiment of the method for uploading a data record to a cloud data repository.

FIG. 5 shows a third embodiment of the method for uploading a data record to a cloud data repository 16. The step of receiving REC-1 a medical data record MDR and the step of selecting SEL a processing plug-in 12.P are identical with the respective steps of the second embodiment displayed and explained in FIG. 4.

In this third embodiment, the step of generating GNR-1 an anonymized data records ADR involves both the processing plug-in 12.P and the core module 11, wherein the processing plug-in 12.P implements the overall functionality for generating GEN an anonymized data records ADR based on the medical data record MDR, and wherein the core module 11 provides a functionality for anonymizing single data items according to a anonymization level parameter. For example, the core module can provide a function func anonymize (string data, int level) as string, which returns an anonymized string of the input string "data" based on the anonymization level. For example, this function can accept the input values 0, 1, 2 and 3 for the anonymization level "level": If the anonymization level is 0, the function returns the input string "data" as a result of the function; if the anonymization level is 1, the function returns the input string "data" symmetrically encrypted with an internal key phrase (so that a deanonymization can be done based on the internal key phrase); if the anonymization level is 2, the function returns a hash of the input string "data" (so that the deanonymization can only be done by a look-up table); if the anonymization level is 3, the function returns an empty string (so that no deanonymization can be done at all).

The processing plug-in 12.P reads the medical data record MDR and splits the medical data record MDR into single data items. Examples for such single data items are the name of the patient, the age of the patient, the sex of the patient, or the single medical examination results (e.g. medical images) contained in the medical data record MDR. The processing plug-in 12.P can then use the anonymization function of the core module 11 to anonymize separately the single data items, alternatively it can create a string containing several data items and use the anonymization function of the core module 11 to anonymize the whole string. The processing plug-in 12.P can for example form a string containing the name, the age and the sex of the patient ("John Doe, 45, m"), which will be anonymized by the core module 11.

The anonymization level parameter the processing plug-in 12.P provides to the core module 11 can be a property of the processing plug-in 12.P (e.g. because the remote application 17.P associated with the processing plug-in 12.P needs a certain anonymization level of the personal data), alternatively the anonymization level parameter can be a property of the local medical institution (e.g. if data protection laws in different countries require different anonymization levels), which can be set as a global parameter within the local transmission software 10 or within the local transmission unit 20.

In this third embodiment the step of uploading UPL the anonymized data records ADR by the core module 11 to the cloud data repository 16 is asynchronous (another technical term is "non-blocking"). The core module 11 defines a function func upload_asynch(data) as int, which initiates an asynchronous upload of the provided data, returning an ID of the upload (which can be identical with a link or an URL the uploaded data can be accessed with). This function is non-blocking, so the function returns the ID immediately after calling the function, performing the actual upload of the data in a separate thread. This implies that the processing plug-in 12.P can process other data while the upload of the anonymized data records ADR is not yet finished, e.g. the processing plug-in 12.P can anonymize other medical data records MDR. This asynchronous method is beneficial because upload of data is in general much slower than internal data processing due to the limited bandwidth between the local and the cloud infrastructure.

After the upload is completed, the step of notifying NTF-1 the processing plug-in 12.P about the completion of the uploading UPL by the core module 11 takes place. This notification can be done by sending a message comprising the ID of the upload from the core module 11 to the processing plug-in 12.P. This message can also be send to the processing plug-in 12.P if the processing plug-in 12.P calls a function of the core module 11 which informs the processing plug-in 12.P about the status of the upload with a certain ID. The message can furthermore comprise a parameter describing the status of the upload (e.g. "successful", "in progress", "pending", "aborted"), wherein "successful" means that the anonymized data records ADR was successfully uploaded to the cloud data repository 16, wherein "in progress" means that the upload of the anonymized data records ADR is currently executed, wherein "pending" means that the upload of the anonymized data records ADR has not yet begun (e.g. because other uploads have a higher priority), and wherein "aborted" means that an error occurred during the upload, so that the upload was not successful.

There can also be the optional step of notifying NTF-2 the remote application 17.P associated with the processing plug-in 12.P of the completion of the uploading UPL. This step of notifying NTF-2 can be realized by sending a message from the core module 11 or from the processing plug-in 12.P to the remote application 17.P associated with the processing plug-in 12.P, e.g. using an API call.

Figure 6:
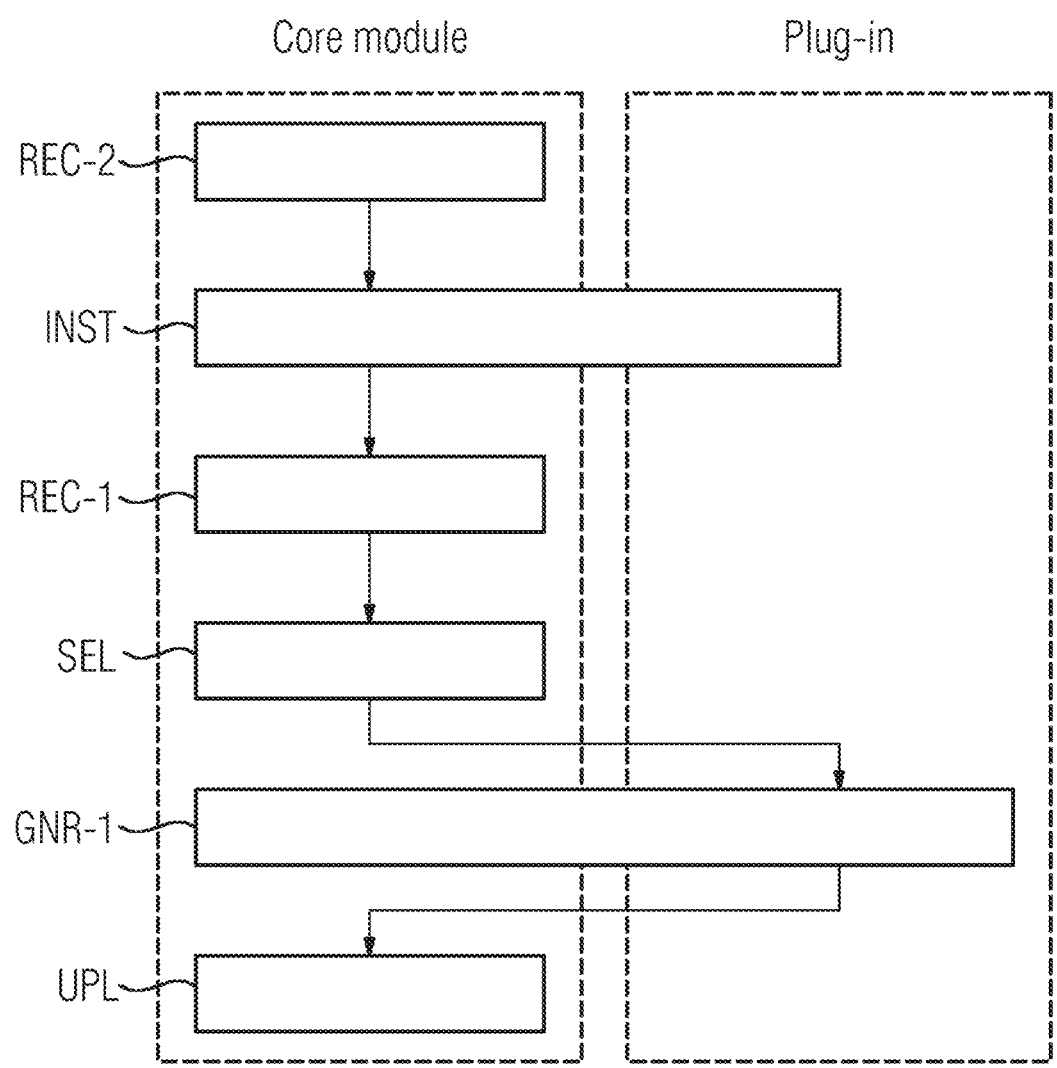
FIG. 6 shows a flowchart of a fourth embodiment of the method for uploading a data record to a cloud data repository.

FIG. 6 shows a fourth embodiment of the method for uploading a data record to a cloud data repository 16. The steps of receiving REC-1, selecting SEL, generating GNR-1 and uploading UPL are identical with respective the steps of the third embodiment displayed and explained in FIG. 5.

The first step of the displayed fourth embodiment is receiving REC-2 a plug-in installation file by the core module 11, wherein the plug-in installation file comprises an installable plug-in and a configuration file. In particular, the step of receiving REC-2 is performed by the input interface 21.1. In the displayed fourth embodiment, the plug-in installation file is loadable into a storage unit 23 of a local transmission unit 20 and comprises program code sections to make the local transmission unit install the installable plug-in as an additional available plugin based on the configuration file, when the plug-in installation file is executed in the local transmission unit 20.

In this fourth embodiment, the plug-in installation file is located in a public repository to which the local transmission software 10, in particular the core module 11, has access. This public repository can comprise several plug-in installation files for different installable plug-ins. In this fourth embodiment, the core module 11 checks in a predefined time-interval (e.g. every day) whether new or altered plug-in installation files are located in the public repository, and in case of affirmation installs the installable plug-in contained in the new or altered plug-in installation file. The public repository can be identical with the cloud data repository 16, but in general the public repository is different from the cloud data repository 16. Alternatively, a plug-in installation file can also be sent to the core module 11, e.g. manually by a user or by an external plug-in distribution service.

The installable plug-in can be a new plug-in 12.1, 12.2, 12.P configured to extend the functionality of an existing local transmission software 10. Alternatively, the installable plug-in can be configured to replace one of the available plug-ins 12.1, 12.2, 12.P. By using such a replacement installation an update mechanism of the available plug-ins 12.1, 12.2, 12.P is realized.

The second step of the displayed fourth embodiment is installing INST the installable plug-in as an additional available plugin 12.1, 12.2, 12.P within the local transmission software 10 based on the configuration file. In particular, the step of installing INST is performed by the core module 11 executed on the calculation unit 22, in particular also involving the memory unit 23. In particular, the installable plug-in will be installed in a memory unit 23 of the local transmission unit 20 hosting the local transmission software 10. In this case, the configuration file defines which file formats the installable plug-in can process. This information can be used by the core module 11 e.g. in the step of selecting SEL a processing plug-in 12.P from the available plug-ins 12.1, 12.2, 12.P.

The step of installing INST can comprise the compilation of source code contained in the plug-in installation file by the calculation unit 22 of the local transmission unit 20. Alternatively, the installable plug-in is contained as an executable file, which can be copied to the memory unit 23 of the local transmission unit 20.

Figure 7:
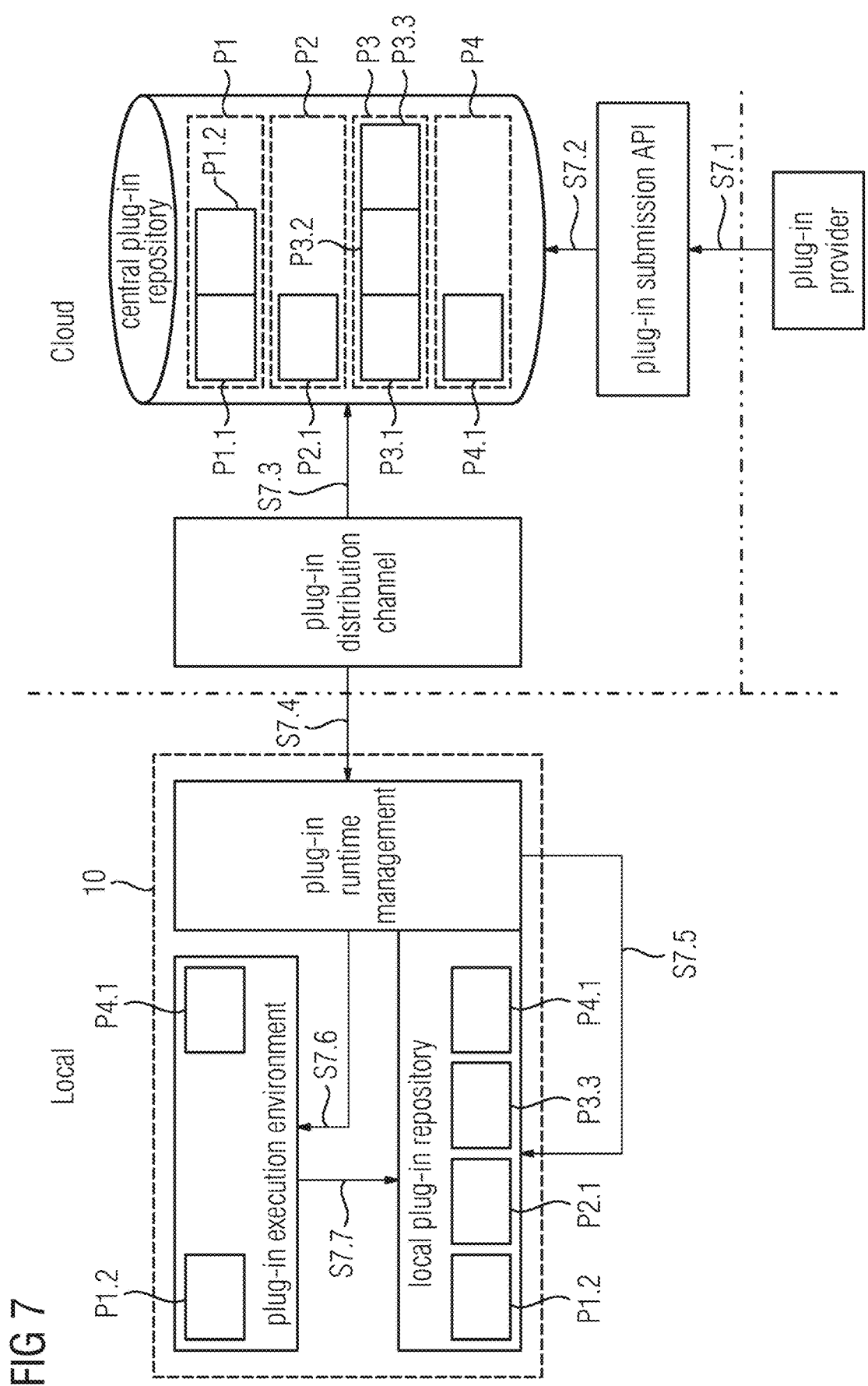
FIG. 7 shows a software architecture implementing the fourth embodiment of the method for uploading a data record to a cloud data repository.

FIG. 7 displays an example of a software architecture configured to implement the fourth embodiment of the method displayed in FIG. 6. A "plug-in provider", which is an entity that develops and/or provides an installable plug-in 12.1, 12.2, 12.P, uploads S7.1, S7.2 a plug-in installation package by using a "plug-in submission API" to a "central plug-in repository". For this purpose the "plug-in submission API" provides a method for uploading a plug-in installation package, which takes at least the plug-in installation package as an parameter, and stores S7.2 the a plug-in installation package within the "central plug-in repository". In particular, the "plug-in submission API" is a cloud application, and the "central plug-in repository" is a cloud storage.

The "central plug-in repository" is configured to store several versions of plug-ins. In the displayed embodiment, there are four plug-ins stored within the "central plug-in repository". For the first plug-in P1 there are two different versions P1.1 and P1.2, for the second-plug-in there is only one version P2.1, for the third plug-in P3 there are three different versions P3.1, P3.2 and P3.3, and for the fourth plug-in P4 there is only one version P4.1. The different versions can be updates for the plug-ins, so that only the newest version is used, and all older versions are obsolete. Alternatively the updates are configured to work with different software products or versions within the local hospital environment (e.g. with different types of PACS).

The "plug-in distribution channel", which is a cloud application, accesses S7.3 the "central plug-in repository" and distributes S7.4 the plug-in installation files to a "plug-in runtime management", which is a local application. The "plug-in distribution channel" is in this embodiment a part of the cloud transmission software 15, and the "plug-in runtime management" is part of the core module 11 of the local transmission software 10.

The "plug-in runtime management" installs S7.5 the plug-ins within a "local plug-in repository", which is also part of the core module 11 of the local transmission software 10. The "local plug-in repository" stores the installed plug-ins, and the "local plug-in repository" can be hosted inside a memory unit 23 of the local transmission unit 20. The installation S7.5 can comprise compilation of source code and/or copying executable files within a memory unit 23.

The "plug-in runtime management" furthermore initializes S7.6, INIT plug-ins by causing the "plug-in execution environment" to get S7.7 a plug-in from the "local plug-in repository" and to start the the plug-in. The "plug-in runtime management" can furthermore terminate TERM plug-ins by causing the "plug-in execution environment" to stop the the plug-in. In the displayed embodiment, the versions P1.2 and P4.1 of the plug-ins P1 and P4 are actually running within the "plug-in execution environment".

Figure 8:
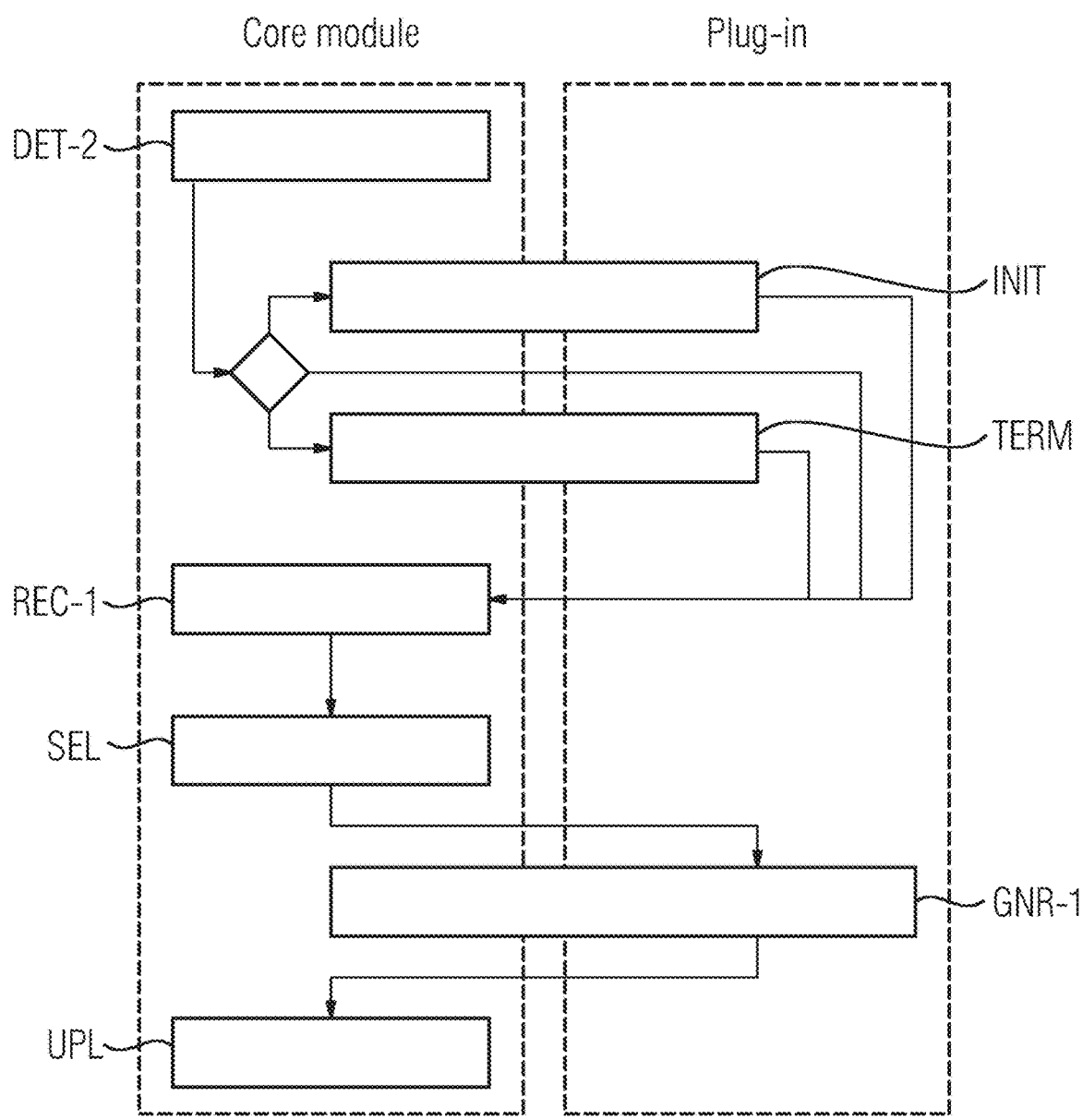
FIG. 8 shows a flowchart of a fifth embodiment of the method for uploading a data record to a cloud data repository.

FIG. 8 shows a fifth embodiment of the method for uploading a data record to a cloud data repository 16. The steps of receiving REC-1, selecting SEL, generating GNR-1 and uploading UPL are identical with the respective steps of the third embodiment displayed and explained in FIG. 5.

The first step of the displayed fifth embodiment is determining DET a resource parameter of a local transmission unit 20 hosting the local transmission software 10, wherein the resource parameter is based on the memory usage and/or the processor usage of the local transmission unit. In particular, the step of determining DET is performed by the core module 11 executed on the calculation unit 22. In this fifth embodiment, the memory usage is the ratio of memory used within the memory unit 23 of the local transmission unit 20 and the total available memory within the memory unit 23 of the local transmission unit. In particular, the ratio is calculated with respect to random access memory (RAM) of the local transmission unit 20 or of the memory unit 23. In this fifth embodiment, the processor usage is the ratio of processing steps executed by the calculation unit 22 of the local transmission unit 20 in a certain time interval and the maximal number of processing steps executable by the calculation unit 22 in the the time interval. In this fifth embodiment, the resource parameter is a pair comprising the memory usage and the processor usage. Alternatively, the resource parameter can be equivalent to the memory usage, or the resource parameter can be equivalent to the processor usage.

The second step of the displayed fifth embodiment depends on a comparison of the resource parameter with a lower resource threshold and an upper resource threshold. In this fifth embodiment, both the lower resource threshold and the upper resource threshold are pairs comprising a memory threshold and a processor threshold. If the processor usage is below the processor threshold of the lower resource threshold, and/or if the memory usage is below the memory threshold of the lower resource threshold, the second step of the displayed fifth embodiment is initializing INIT a first plug-in of the available plug-ins 12.1, 12.2, 12.P. If the processor usage is above the processor threshold of the upper resource threshold and/or if the memory usage is above the memory threshold of the upper resource threshold, the second step of the displayed fifth embodiment is terminating TERM a second plug-in of the available plug-ins 12.1, 12.2, 12.P. If none of the the two conditions is fulfilled, there is neither a step of initializing INIT nor a step of terminating TERM in the displayed fifth embodiment. If the resource parameter is based only on the memory usage or only on the processor usage, also the upper and the lower threshold are based on this one-dimensional quantity, and the comparison is based on this one-dimensional quantity. In particular, the step of initiating INIT and/or terminating TERM are performed by the core module 11 executed on the calculation unit 22.

In this fifth embodiment, the termination of a second plug-in is equivalent to terminate the process corresponding to the second plugin on the local transmission unit 20. Alternatively, the termination can also imply transferring the second plug-in to a pause mode, wherein the first plug-in and the second plug-in cause less memory usage and/or processor usage in the pause mode than in a normal operation mode.

In this fifth embodiment, the initialization of a first plug-in is equivalent to initialize a process corresponding to the first plugin on the local transmission unit 20. Alternatively, the termination can also imply transferring the first plug-in from pause mode to normal operation mode.

The step of terminating TERM a second plug-in of the available plug-ins 12.1, 12.2, 12.P is in this fifth embodiment executed by the core module 11 by sending a termination message to the second plug-in. The termination message can alternatively be sent to the operating system hosting the core module 11 and the available plug-ins 12.1, 12.2, 12.P.

The step of initializing INIT a first plug-in of the available plug-ins 12.1, 12.2, 12.P is in this fifth embodiment executed by the core module 11 by sending an initialization message to the operating system hosting the core module 11 and the available plug-ins 12.1, 12.2, 12.P. If the first plug-in is in pause mode, the step of initializing can also be executed by the core module 11 by sending an initialization message to the directly to the first plug-in.

Figure 9:
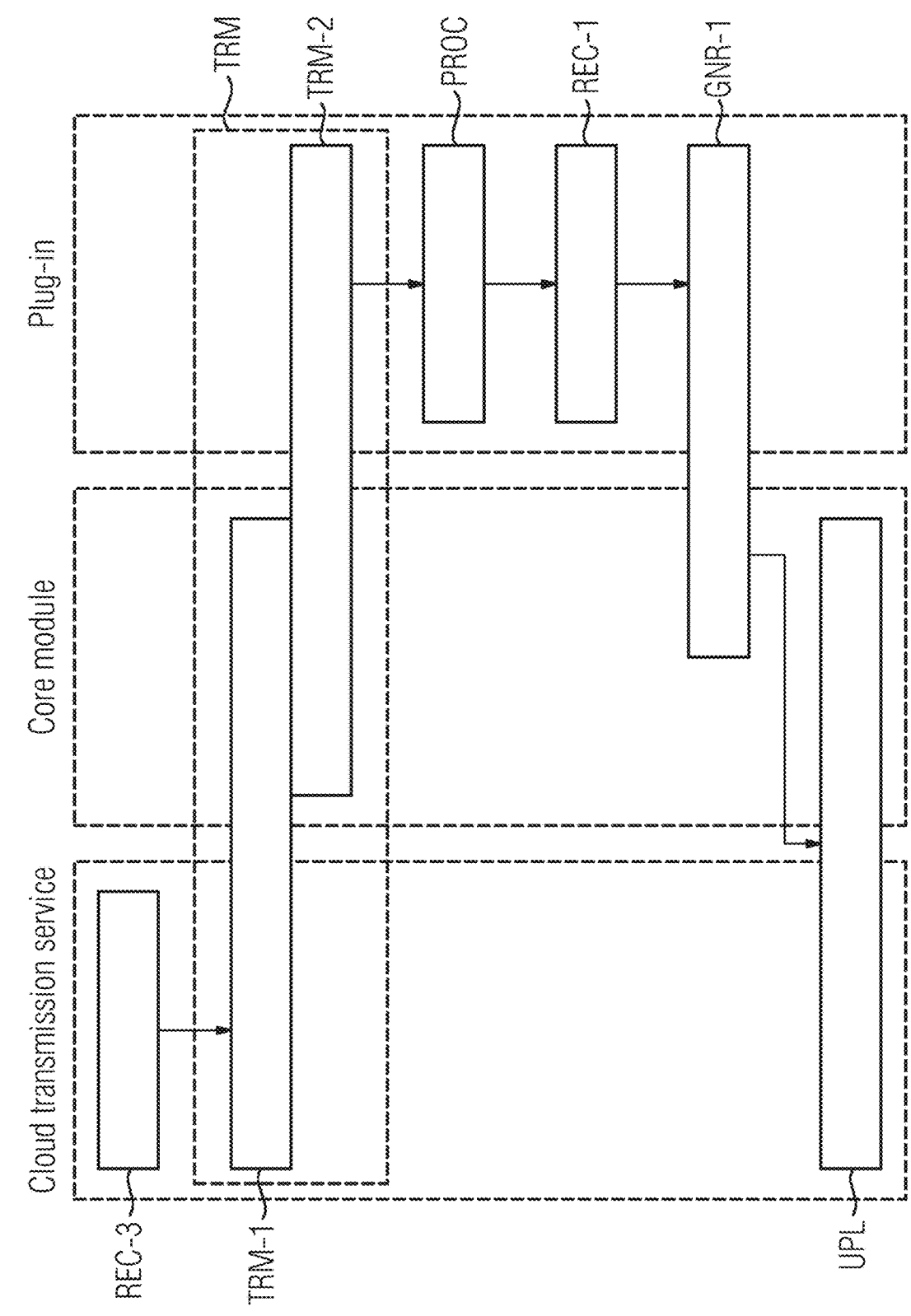
FIG. 9 shows a flowchart of a sixth embodiment of the method for uploading a data record to a cloud data repository.

FIG. 9 shows a sixth embodiment of the method for uploading a data record to a cloud data repository 16. The steps of receiving REC-1 is identical with the respective step of the first embodiment displayed and explained in FIG. 3, the step of generating GNR-1 is identical with the respective step of the third embodiment displayed and explained in FIG. 5. The step of UPL is identical with the respective step of the third embodiment displayed and explained in FIG. 5, wherein in FIG. 9 additional the involvement of a cloud transmission software 15 is displayed.

The first step of the displayed sixth embodiment is receiving REC-3 an action message from the remote application 17.1, 17.2, 17.P by a cloud transmission software 15, wherein the action message comprises a plug-in identifier. The action message is advantageously received from the remote application 17.1 associated with the receiving plug-in; alternatively the action message can also be received from another remote application 17.1, 17.2, 17.P. In this sixth embodiment, the receiving plug-in 12.1 differs from the processing plug-in 12.P; alternatively the receiving plug-in 12.1 and the processing plug-in 12.P are identical. The action message comprises an instruction to be executed by the receiving plugin 12.1. A first example for an action message is the instruction to search for new medical data records MDR in the local repository 14.1 associated with the receiving plugin 12.1. A second example for an action message is the instruction to store a processed data record PDR in the local repository 14.1 associated with the receiving plugin 12.1.

The second step of the displayed sixth embodiment is transmitting TRM the action message from the cloud transmission software 15 through the core module 11 to the receiving plug-in 12.1, wherein the receiving plug-in 12.1 is one of the available plug-ins 12.1, 12.2, 12.P, and wherein the receiving plug-in 12.1 is selected by the core module 11 based on the plug-in identifier. In particular, the step of transmitting TRM is performed by the core module 11 and the receiving plug-in 12.1 executed on the calculation unit 22, in particular involving the input interface 21.1. In the displayed sixth embodiment, the step of transmitting TRM comprises a sub-step of transmitting TRM-1 the action message from the cloud transmission software 15 to the core module 11, and a sub-step of transmitting TRM-2 the the action message from the core module 11 to the receiving plug-in 12.1. In this sixth embodiment, the plug-in identifier is a unique identifier which discriminates the receiving plug-in 12.1 from the other available plug-ins 12.2, 12.P, e.g. the name of the receiving plug-in 12.1 or a unique string or integer associated with the receiving plug-in 12.1.

The third step of the displayed sixth embodiment is processing PROC the action message by the receiving plug-in 12.1. In particular, the step of processing PROC is performed by the core module 11 executed on the calculation unit 22. If the action message is, for example, the instruction to search for new medical data records MDR in the local repository 14.1 associated with the receiving plugin 12.1, the search for new medical data records MDR is performed by the receiving plugin 12.1. If the action message is, for example, the instruction to store a processed data record PDR in the local repository 14.1 associated with the receiving plugin 12.1, the processed data records PDR is stored in the local repository 14.1 associated with the receiving plugin 12.1 by the receiving plugin 12.1.

Figure 10:
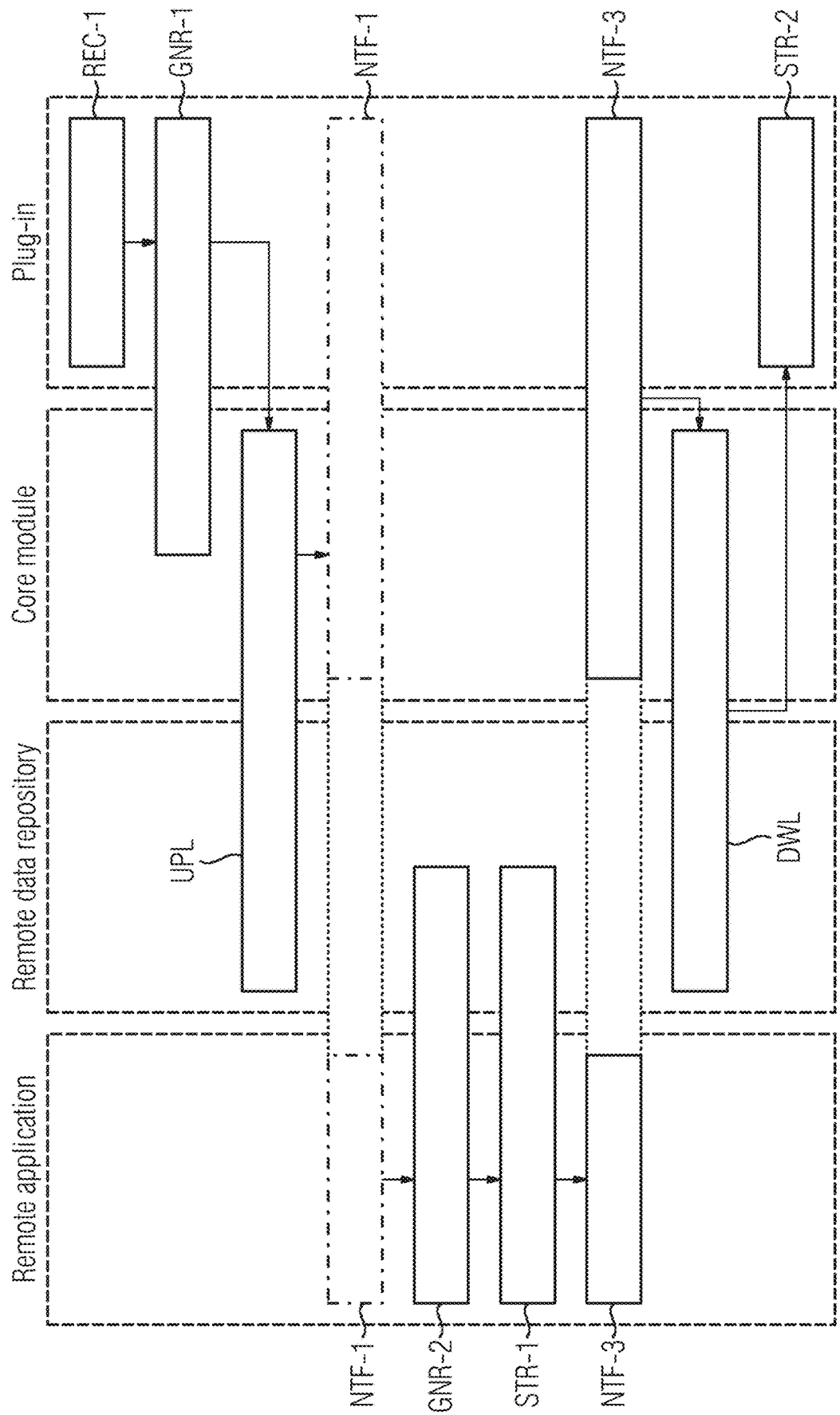
FIG. 10 shows a flowchart of a seventh embodiment of the method for uploading a data record to a cloud data repository.

FIG. 10 displays a seventh embodiment of the method for uploading a data record to a cloud data repository 16. The steps of receiving REC-1 is identical with the respective step of the first embodiment displayed and explained in FIG. 3, the step of generating GNR-1 is identical with the respective step of the third embodiment displayed and explained in FIG. 5. The step of UPL is identical with the respective step of the third embodiment displayed and explained in FIG. 5.

In this seventh embodiment, the medical data record MDR comprises a first data item D.1 and a second data item D.2, wherein the first data item D.1 comprises personal data of a patient, and wherein the second data item D.2 is three-dimensional imaging data of a tomographic examination (e.g. by a computed tomography apparatus or a magnetic resonance apparatus). Of course it is also possible to use other medical data as the second data item D.2. The anonymized data records ADR comprises a data record identifier AD and the second data item D.2, wherein the data record identifier AD is a hash of the first data item D.1, so that the first data item D.1 cannot be calculated from the data record identifier AD. A mapping from the data record identifier AD to the first data item D.1 is stored within the plug-in-specific storage 13.P associated with the processing plug-in 12.P An advantageous, optional step of the displayed seventh embodiment is notifying NTF-1 by the core module 11 the processing plug-in 12.P about the completion of the uploading UPL. As an alternative to this step, the processing plug-in 12.P can regularly check the cloud data repository 16 for new anonymized data records ADR, e.g. every minute or every hour.

The next step of the displayed seventh embodiment is generating GNR-2 a processed data record PDR based on the anonymized data records ADR by the remote application 17.P associated with the processing plug-in 12.P. In this embodiment the processed data record PDT comprises the data record identifier and a processed second data item PD.2. Here the processed second data item PD.2 is a sophisticated visualization of the imaging data contained in the second data item D.2 of the anonymized data records ADR, e.g. by a CPU-intensive rendering, which can be executed faster and/or cheaper within the cloud. Also other methods for transforming the anonymized data records ADR into a processed data record PDR are possible, e.g. generating a recommendation of action determined with an intelligent algorithm, or finding data records similar to the anonymized data records ADR for comparison reasons within the cloud data repository 16.

The next step of the displayed seventh embodiment is storing STR-1 the processed data record PDR in the cloud data repository 16 by the remote application 17.P associated with the processing plug-in 12.P. In particular, the processed data record PDR can be stored in within a sub-repository 16.P associated with the remote application 17.P associated with the processing plug-in 12.P. Here the storing STR-1 relies on a call of the remote application 17.P associated with the processing plug-in 12.P to an API of the cloud data repository 16.

The next step of the displayed seventh embodiment is notifying NTF-3 the local transmission software 10 about the storing STR-1 of the processed data record PDR by sending a message from the remote application 17.P associated with the processing plug-in 12.P to the local transmission software 10. In this embodiment, the notifying NTF-3 is done by sending a message from the remote application 17.P associated with the processing plug-in 12.P to the core module 11, which forwards the message the to the processing plug-in 12.P. The message comprises the storage location of the processed data record PDR, in particular a link that can be used to access the processed data record PDR, or an identifier of the processed data record PDR which can be used in an API call to the cloud data repository.

The next step of the displayed seventh embodiment is downloading DWL the processed data record PDR from the cloud data repository 16 by the processing plug-in 12.P; the last step is storing STR-2 the processed data record PDR within a local data repository 14.1, 14.2, 14.P by the processing plug-in 12.P (e.g. based on the link contained in the message). In particular, the steps of downloading DWL and storing STR-2 are performed by the processing plug-in 12.P executed on the calculation unit 22, in particular involving the input interface 21.1 and/or the output interface 21.2. The split of the transfer of the processed data record PDR into notifying NTF-3 by a message and downloading DWL the processed data record PDR is advantageous, because the file size of the message is in general much smaller than the file size of the processed data record PDR (which in this embodiment comprises a visualization of DICOM data). Such messages can then directly be used within message queuing, which in general have a hard limit on the size of messages. In this seventh embodiment the processed data record PDR is stored within the local data repository 14.P associated with the processing plugin 12.P, which is a PACS ("Picture Archiving and Communication System"). In this embodiment, by the use of the mapping between first data items D.1 and data record identifiers AD stored in the plug-in-specific storage 13.P associated with the processing plug-in 12.P, the data record identifier AD contained in the processed data record PDR can be mapped again to the first data item D.1, which contains personal data. So the processing plug-in 12.P can generate a processed medical data record PMDR comprising the first data item D.1 and the processed second data item PD.2, which can be saved in the local data repository 14.P associated with the processing plugin 12.P.

By this embodiment, it is possible to process medical data records MDR using cloud resources according to data privacy regulations, since the personal data of the first data item D.1 is never transmitted to the cloud and/or outside of the hospital or the hospital group.

Figure 11:
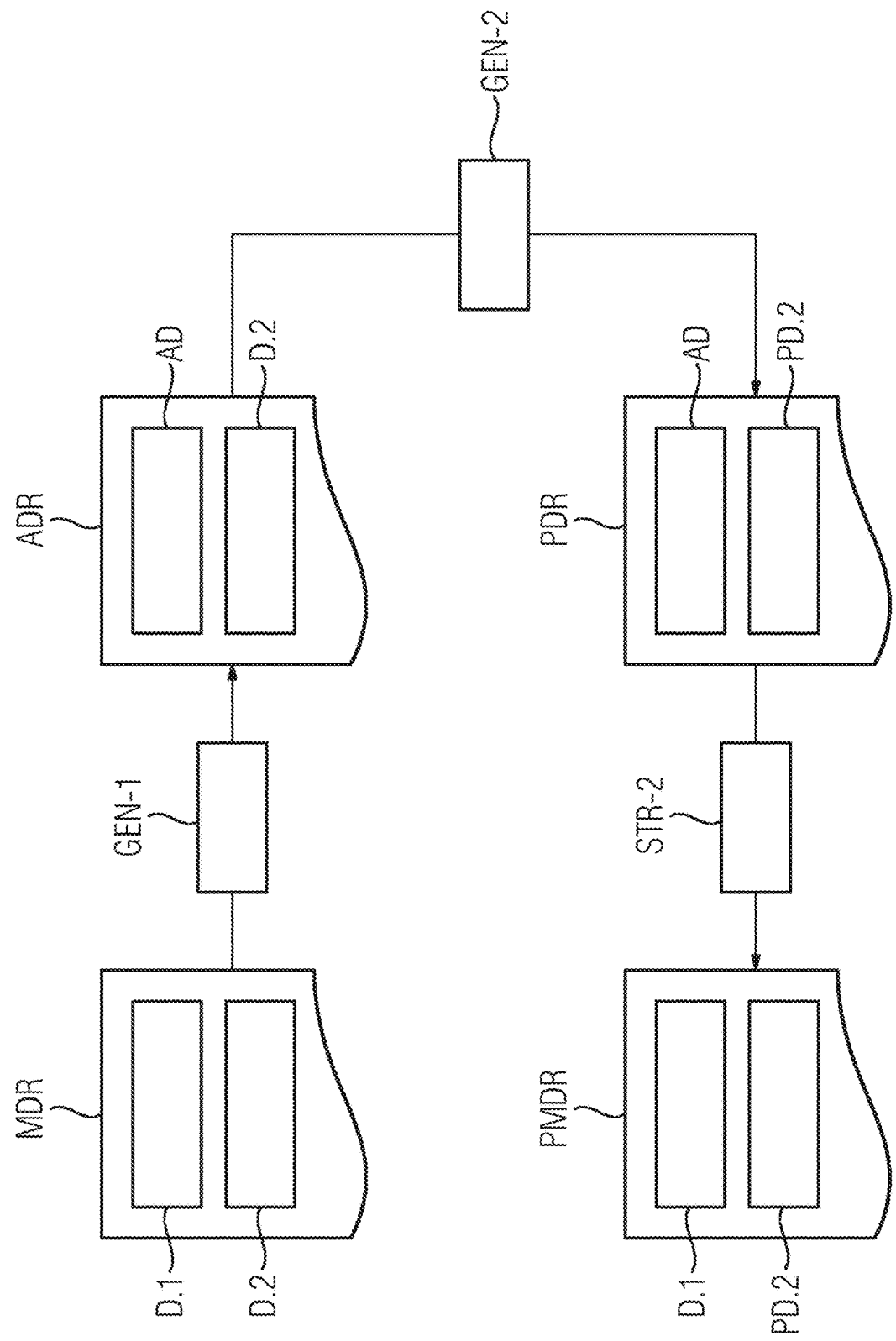
FIG. 11 shows a software architecture implementing the seventh embodiment of the method for uploading a data record to a cloud data repository.

FIG. 11 displays the different data records in the seventh embodiment of the method for uploading a data record displayed in FIG. 10. The medical data record MDR comprises a first data item D.1 and a second data item D.2, wherein the first data item D.1 comprises personal data related to a patient, and wherein the second data item D.2 comprises results of a medical examination of the patient, e.g. medical imaging data. By the step of generating GNR-1 an anonymized data record ADR is created based on the medical data record MDR. The anonymized data records ADR comprises the second data item D.2 and a data record identifier AD, wherein the data record identifier AD is based on the first data item D.1. In particular the first data item D.1 cannot be reconstructed from the data record identifier AD. The medical data record MDR and the anonymized data record ADR are also the relevant data records for the other embodiments of the method for uploading a data record and the other methods. By the step of generating GNR-2 a processed data record PDR is created, wherein the processed data record PDR comprises the data record identifier AD and a processes second data item PD.2, wherein the processed second data item PD.2 is based on the second data item D.2. By the step of storing STR-2 the processed data record PDR within a local data repository 14.1, 14.2, 14.P a processed medical data record PMDR is created, wherein the processed medical data record PMDR comprises the first data item D.1 and the processed second data item PD.2.

Figure 12:
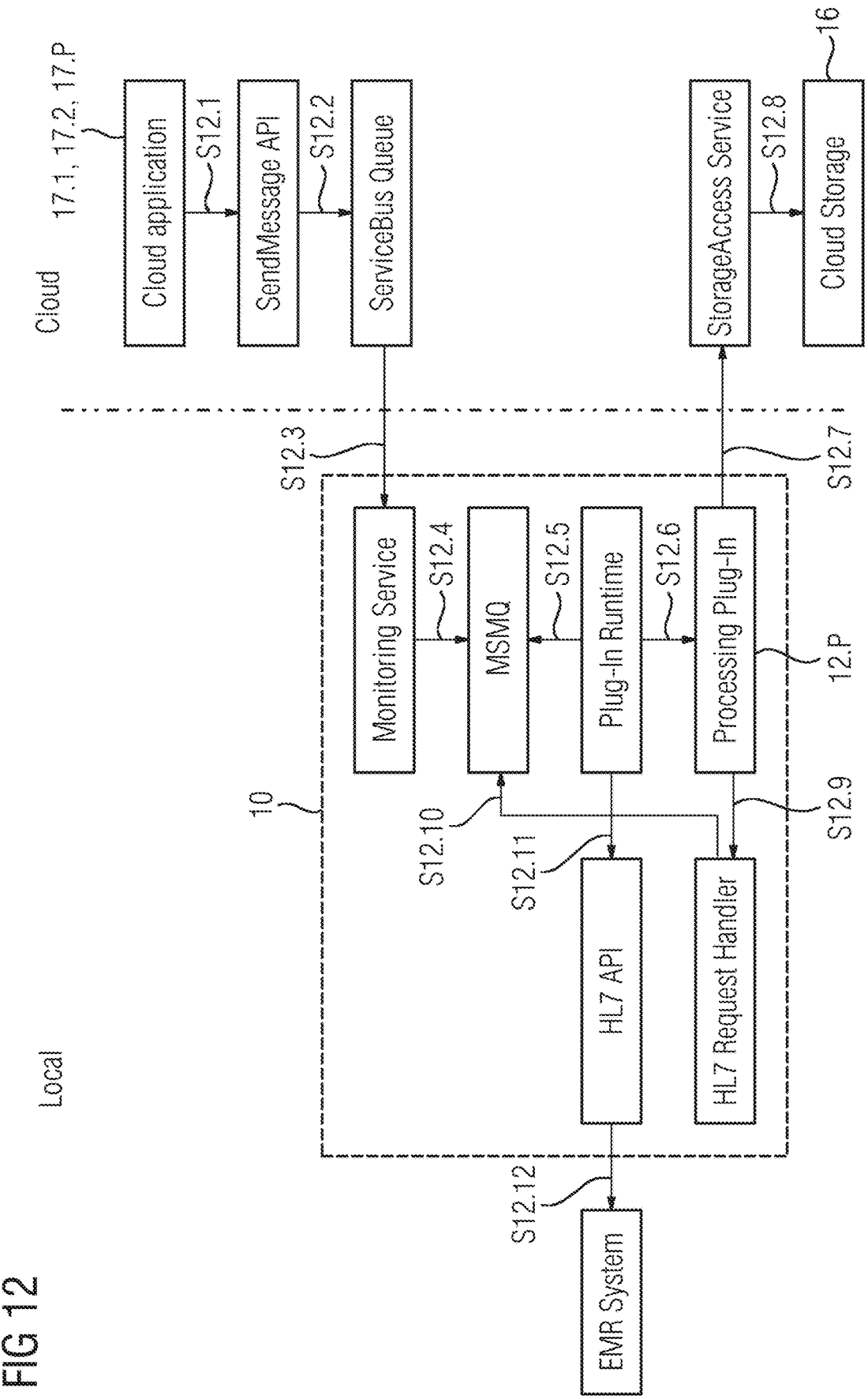
FIG. 12 shows the data structure of a medical data record and a anonymized data record.

FIG. 12 displays a more detailed view of the step of receiving REC-3 an action message from the remote application 17.1, 17.2, 17.P, the step of transmitting TRM the action message from the cloud transmission software 15 through the core module 11 to a receiving plug-in 12.1, 12.2, 12.P and the step of processing PROC the action message by the receiving plug-in 12.1, 12.2, 12.P in the case of the action message being an instruction to store a processed data record PDR in the local repository 14.1, 14.2, 14.P associated with the receiving plugin 12.1, 12.2, 12.P.

The remote application 17.1, 17.2, 17.P here invokes S12.1 a "SendMessage API" of the cloud transmission software 15. This API is configured to receive messages of different format and to initiate the processing of the received messages, here the message comprises metadata of the processed data record PDR, in particular a link to a processed HL7 data file located in the cloud data repository 16. In order to process the message the "SendMessage API" enqueues S12.2 the received message into the "ServiceBus queue" of the cloud transmission software 15. This queue works according to the FIFO (acronym for "first in, first out") principle to store messages that need to be transmitted to the local transmission software 10, so that the performance of the cloud transmission software 15 is not restricted by the bandwidth of the data connection between the cloud transmission software 15 and the local transmission software 10.

The "ServiceBus queue" triggers S12.P a "Monitoring service" of the core module 11 of the local transmission software 10. This "Monitoring Service" is configured to receive messages or other interaction processes from the cloud transmission software 15, and to enqueue S12.4 the received messages or other interaction processes into a "MSMQ" (acronym for "Microsoft MessageQueue", alternatively other implementation of message queues can be used). The usage of this second queue has the advantage that both the downloading process by the local transmission software 10 and the further processing steps by the local transmission software 10 are also non-blocking.

The "Plugin runtime" is then responsible to dequeue S12.5 the message form the "MSMQ" according e.g. the FIFO principle or according to the priority of the messages and to forward S12.6 the message to the correct processing plug-in 12.P. The processing plug-in 12.P uses the metadata (the link to the processed HL7 data record) to call S12.7 the "StorageAccess Service" in order to access and download S12.8 the processed HL7 data record to a local data storage.

The processing plug-in 12.P calls S12.9 the "HL7 Request Handler" to enqueue S12.10 an action message into the "MSMQ". The "Plug-In Runtime" dequeues S12.6 the action message, which instructs the "Plug-In Runtime" to call S12.11 the "HL7 API" in order to store S12.12 the processed HL7 data record within the "EMR-System" (acronym for electronical medical record).

Figure 13:
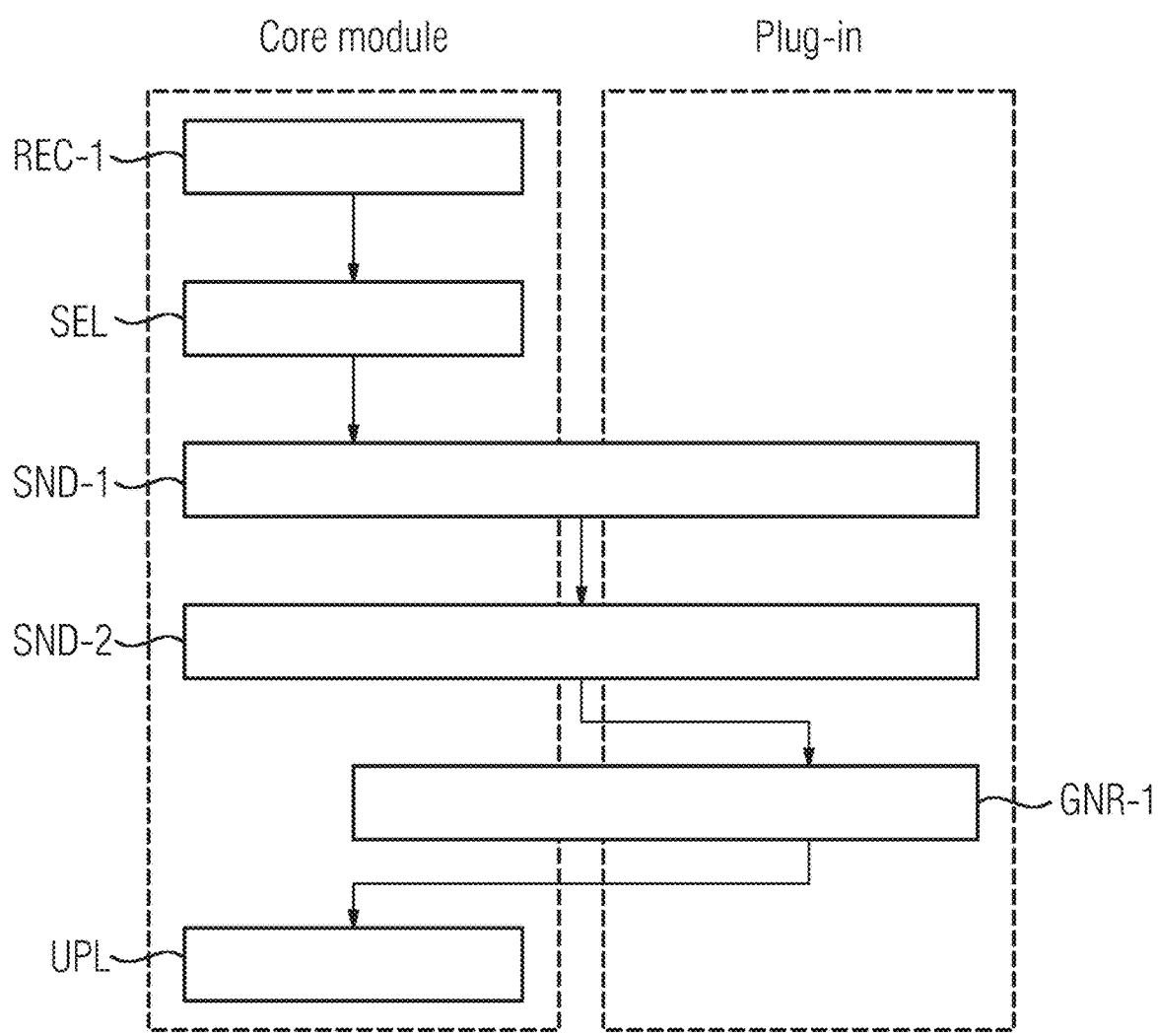
FIG. 13 shows a flowchart of an eighth embodiment of the method for uploading a data record to a cloud data repository.

FIG. 13 shows an eighth embodiment of the method for uploading a data record to a cloud data repository 16. The steps of receiving REC-1, selecting SEL, generating GNR-1 and uploading UPL are identical with the respective steps of the third embodiment displayed and explained in FIG. 5.

The eighth embodiment of the of the method for uploading a data record to a cloud data repository 16 furthermore comprises the step of sending SND-1 a first message from the core module 11 to the processing plug-in 12.P. Here the first message is a status inquiry message prompting the processing plug-in 12.P to report its current status. The message can be send from the core module 11 to the processing plug-in 12.P by calling an API function of the processing plug-in 12.P. It is thinkable that there are different API functions of the processing plug-in 12.P that can be used, e.g. a function for inquiring whether the processing plug-in 12.P is running and successfully loaded by the core module 11, and another function for inquiring whether the processing plug-in 12.P is able to make use of the core module 11 provided services, and do it's expected functionality without any infrastructural problems.

The eighth embodiment of the of the method for uploading a data record to a cloud data repository 16 furthermore comprises the step of sending SND-2 a second message from the processing plug-in 12.P to the core module 11, in response to the step of sending SND-1 a first message from the core module 11 to the processing plug-in 12.P. Here the second message is a status response message containing the current status of the processing plug-in 12.P. The second message is here the return value of the API function of the processing plug-in 12.P.

Figure 14:
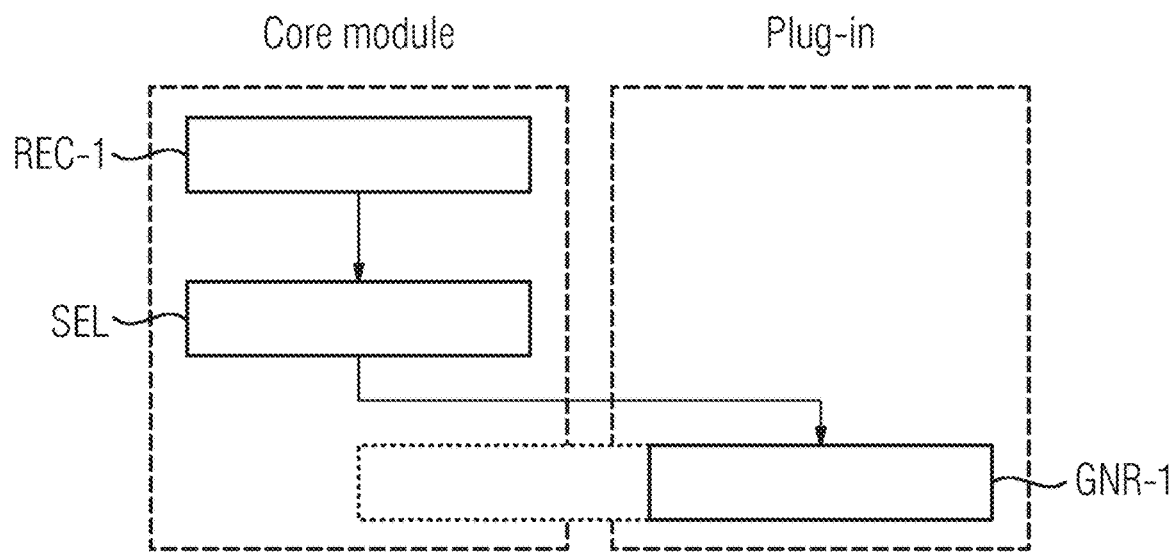
FIGS. 14-17 show flowcharts of embodiments of the method for generating an anonymized data record.

FIG. 14 shows a flowchart of an embodiment of a method for generating an anonymized data records ADR. The displayed embodiment of the method for generating an anonymized data records ADR comprises the step of receiving REC-1 a medical data record MDR by the core module 11 of the local transmission software 10, the step of selecting SEL the processing plug-in 12.P from the available plug-ins 12.1, 12.2, 12.P by the core module 11 based on the medical data record MDR, and the step of generating GNR-1 an anonymized data records ADR based on the medical data record MDR by a processing plug-in 12.P. These steps can comprise the features and advantageous embodiments of the respective steps of the method for uploading a data record displayed in FIG. 4 and/or FIG. 5.

Figure 15:
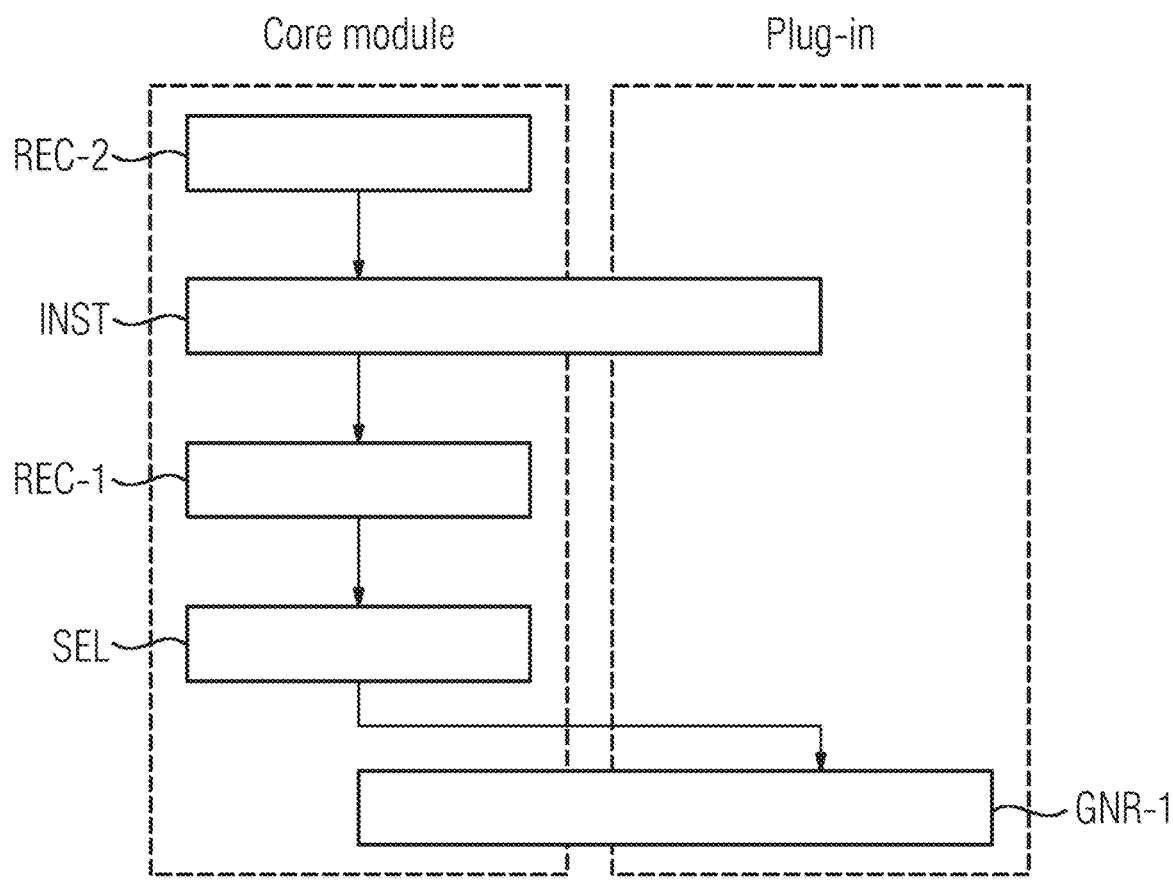

FIG. 15 shows a flowchart of another embodiment of a method for generating an anonymized data records ADR. The displayed embodiment of the method for generating an anonymized data records ADR comprises the steps of the embodiment displayed in FIG. 14, as well as the step of receiving REC-2 a plug-in installation file by the core module 11, wherein the plug-in installation file comprises an installable plug-in and a configuration file and the step of installing INST the installable plug-in as an additional available plugin 12.1, 12.2, 12.P based on the configuration file. These additional steps can comprise the features and advantageous embodiments of the respective steps of the method for uploading a data record displayed in FIG. 6. In particular this embodiment of the method for generating an anonymized data records ADR can use the software architecture displayed in FIG. 6.

Figure 16:
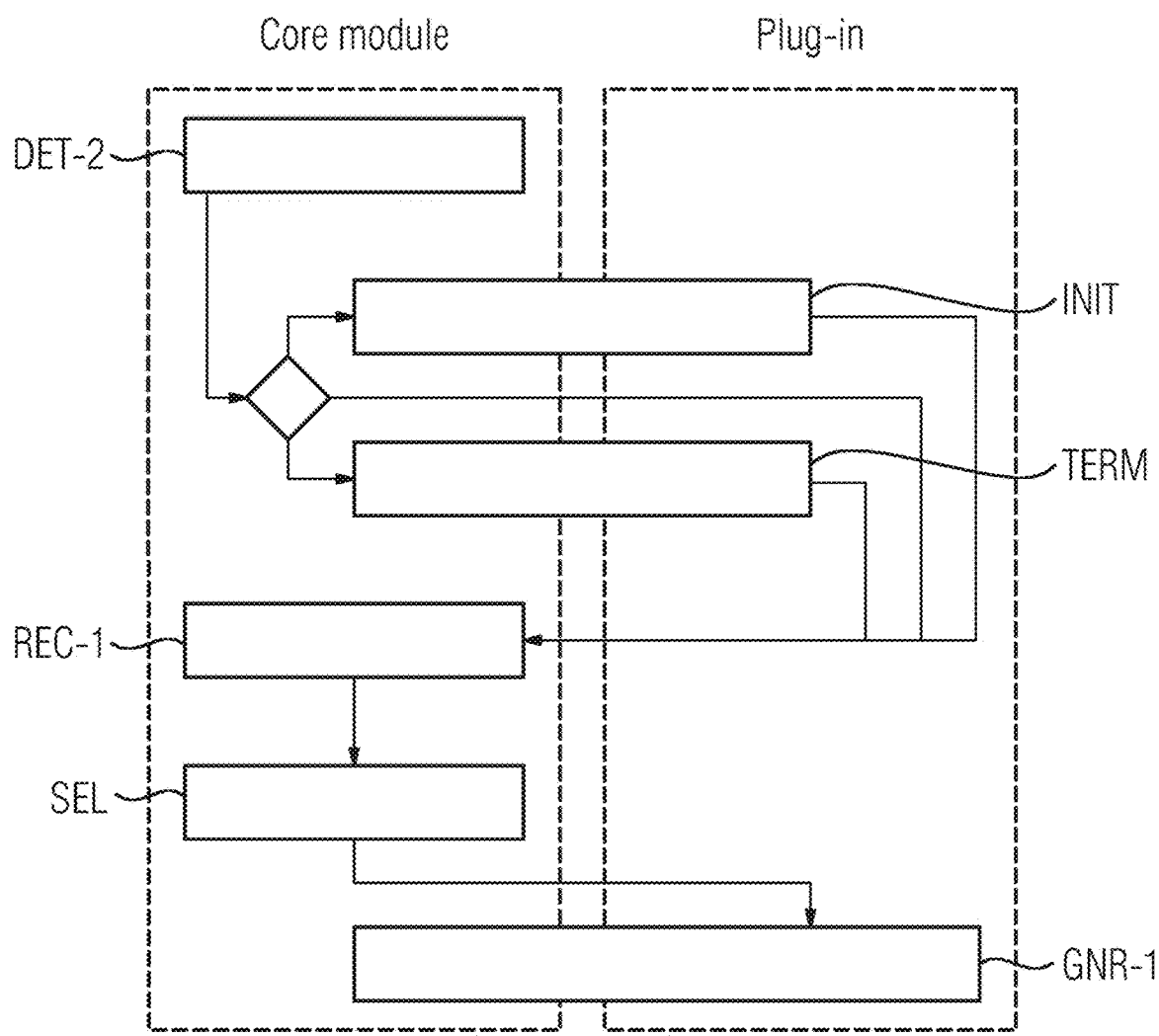

FIG. 16 shows a flowchart of another embodiment of a method for generating an anonymized data records ADR. The displayed embodiment of the method for generating an anonymized data records ADR comprises the steps of the embodiment displayed in FIG. 13, as well as the step of determining DET a resource parameter of a local transmission unit 20 hosting the local transmission software 10, wherein the resource parameter is based on the memory usage and/or the processor usage of the local transmission unit 10; the step of initializing INIT a first plug-in of the available plug-ins 12.1, 12.2, 12.P, if the resource parameter is below a lower resource threshold; and the step of terminating TERM a second plug-in of the available plug-ins 12.1, 12.2, 12.P, if the resource parameter is above an upper resource threshold, wherein the upper resource threshold is higher than the lower resource threshold. These additional steps can comprise the features and advantageous embodiments of the respective steps of the method for uploading a data record displayed in FIG. 8.

Figure 17:
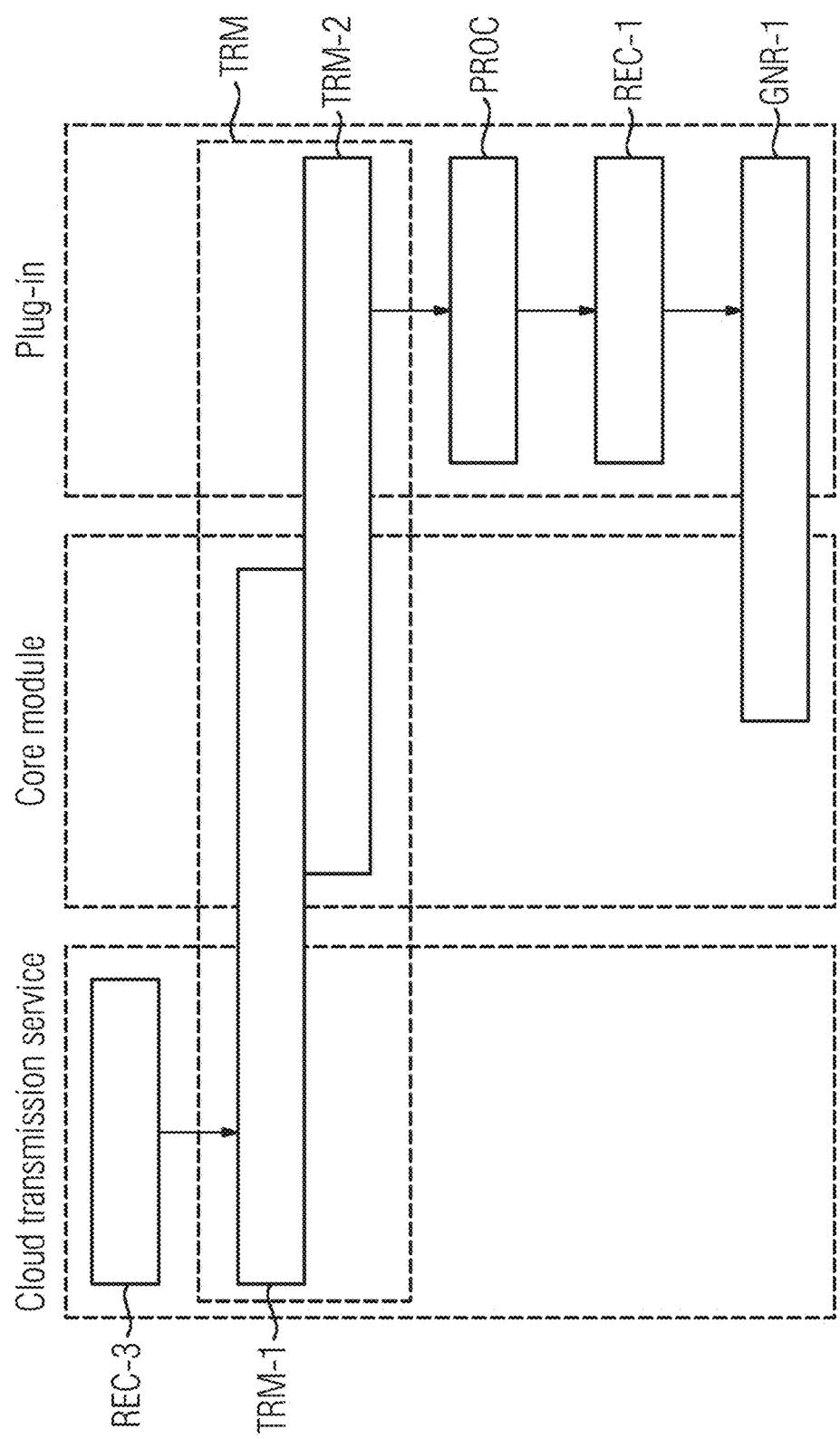

FIG. 17 shows a flowchart of another embodiment of a method for generating an anonymized data records ADR. The displayed embodiment of the method for generating an anonymized data records ADR comprises the steps of the embodiment displayed in FIG. 14, as well as the step of receiving REC-3 an action message from the remote application 17.1, 17.2, 17.P by a cloud transmission software 15, wherein the action message comprises a plug-in identifier; the step of transmitting TRM the action message from the cloud transmission software through the core module to a receiving plug-in 12.1 of the available plug-ins 12.1, 12.2, 12.P, wherein the receiving plug-in 12.1 is selected by the core module 11 based on the plug-in identifier; and the step of processing PROC the action message by the receiving plug-in 12.1. These additional steps can comprise the features and advantageous embodiments of the respective steps of the method for uploading a data record displayed in FIG. 9.

Figure 18:
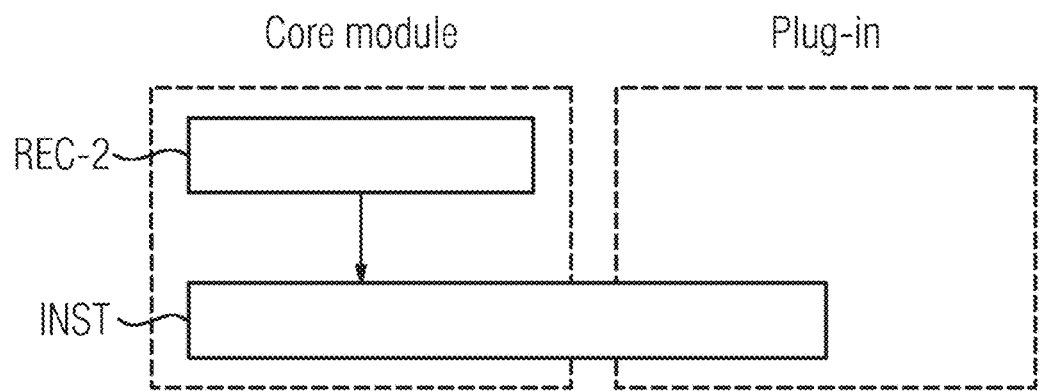
FIG. 18 shows a flowchart of the method for installing an installable plug-in within a local transmission software or within a local transmission unit.

FIG. 18 shows a flowchart of the method for installing an installable plug-in within a local transmission software or within a local transmission unit. The method comprises the step of receiving REC-2 a plug-in installation file by the core module 11, wherein the plug-in installation file comprises an installable plug-in and a configuration file and the step of installing INST the installable plug-in as an additional available plugin 12.1, 12.2, 12.P based on the configuration file. These steps can comprise the features and advantageous embodiments of the respective steps of the method for uploading a data record displayed in FIG. 6. In particular this embodiment of the method for installing an installable plug-in within a local transmission software 10 or within a local transmission unit 20 can use the software architecture displayed in FIG. 6.

Figure 19:
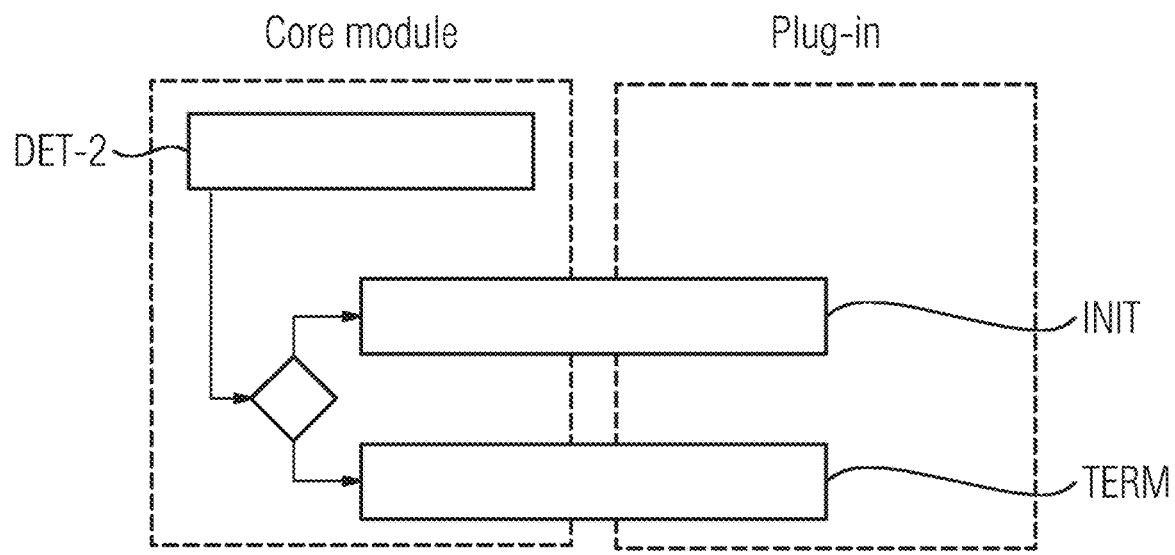
FIG. 19 shows a flowchart of the method for initializing or terminating a plug-in within a local transmission software or a the local transmission unit.

FIG. 19 shows a flowchart of the method for initializing or terminating a plug-in within a local transmission software or a the local transmission unit. The method comprises the step of determining DET a resource parameter of a local transmission unit 20 hosting the local transmission software 10, wherein the resource parameter is based on the memory usage and/or the processor usage of the local transmission unit 10; the step of initializing INIT a first plug-in of the available plug-ins 12.1, 12.2, 12.P, if the resource parameter is below a lower resource threshold; and the step of terminating TERM a second plug-in of the available plug-ins 12.1, 12.2, 12.P, if the resource parameter is above an upper resource threshold, wherein the upper resource threshold is higher than the lower resource threshold. These steps can comprise the features and advantageous embodiments of the respective steps of the method for uploading a data record displayed in FIG. 8.

Figure 20:
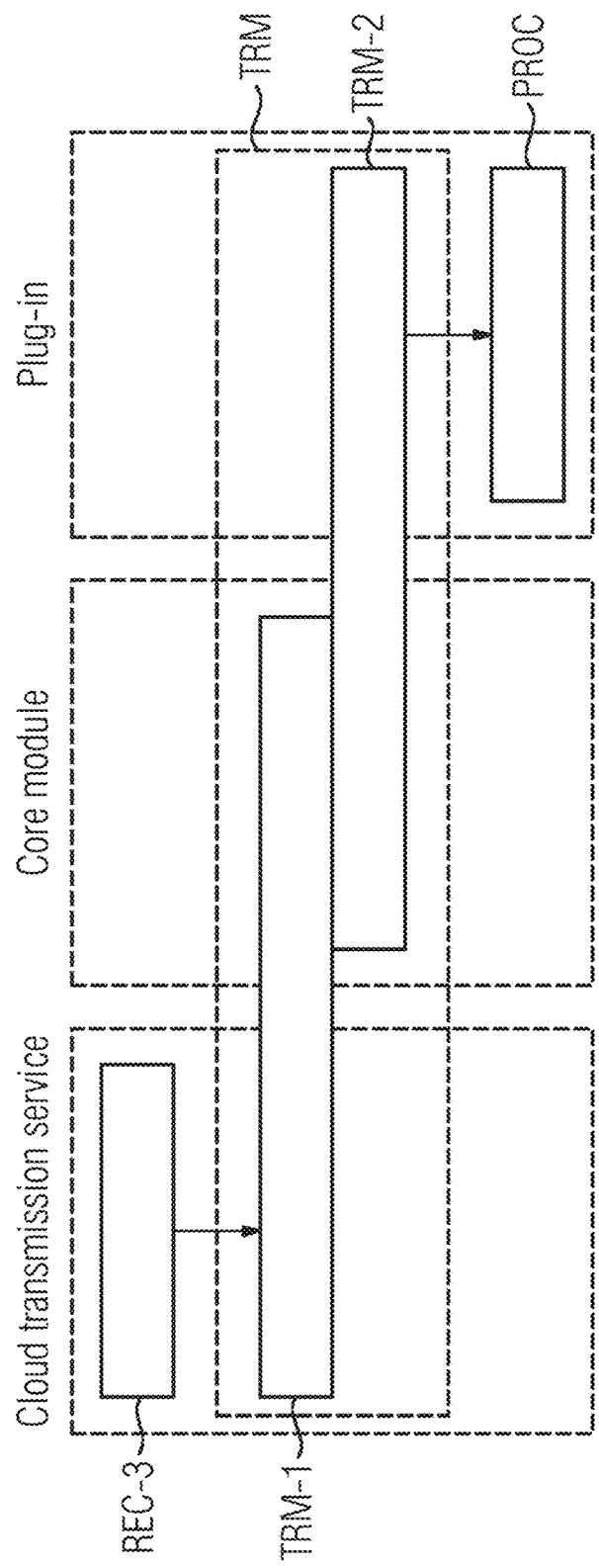
FIG. 20 shows a flowchart of the method for processing an action message within a local transmission software or within a local transmission unit.
Figure 21:
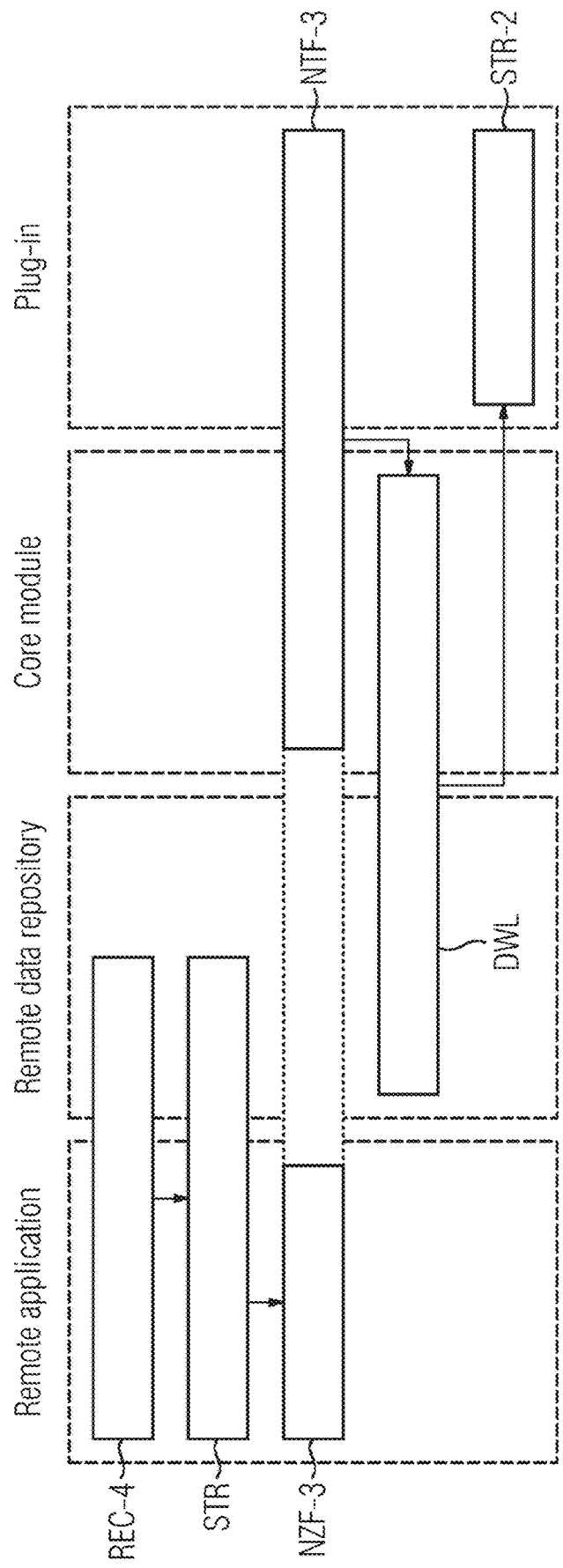
FIG. 21 shows a flowchart of the method for storing a processed medical data record within the local transmission software.

FIG. 20 shows a flowchart of the method for processing an action message within a local transmission software or within a local transmission unit. The method comprises the step of receiving REC-3 an action message from the remote application 17.1, 17.2, 17.P by a cloud transmission software 15, wherein the action message comprises a plug-in identifier; the step of transmitting TRM the action message from the cloud transmission software through the core module to a receiving plug-in 12.1 of the available plug-ins 12.1, 12.2, 12.P, wherein the receiving plug-in 12.1 is selected by the core module 11 based on the plug-in identifier; and the step of processing PROC the action message by the receiving plug-in 12.1. These steps can comprise the features and advantageous embodiments of the respective steps of the method for uploading a data record displayed in FIG. 9. FIG. 21 shows a flowchart of the method for storing a processed medical data record within the local transmission software 10. The method comprises the step of generating GNR-2 a processed data record PDR based on the anonymized data record ADR by the remote application 17.P associated with the processing plug-in 12.P; the step of storing STR-1 the processed data record PDR in the cloud data repository 16 by the remote application 17.P associated with the processing plug-in 12.P; the step of notifying NTF-3 the local transmission software 10 about the storing STR-1 of the processed data record PDR by sending a message from the remote application 17.P associated with the processing plug-in 12.P to the local transmission software 10; the step of downloading DWL the processed data record PDR from the cloud data repository 16 by the processing plug-in 12.P; and the step of storing STR-2 the processed data record PDR within a local data repository 14.1, 14.2, 14.P by the processing plug-in 12.P. These steps can comprise the features and advantageous embodiments of the respective steps of the method for uploading a data record displayed in FIG. 10.

The invention claimed is:

1. A method for uploading a data record to a cloud data repository, the method comprising:
  receiving a medical data record via a local transmission software, the local transmission software including a core module and available plug-ins, each available plug-in among the available plug-ins being associated with a respective remote application among a plurality of remote applications, the plurality of remote applications being configured to access a cloud data repository;
  generating an anonymized data record based on the medical data record via a processing plug-in among the available plug-ins; and
  uploading the anonymized data record to the cloud data repository via the core module, the anonymized data record in the cloud data repository being accessible via a first remote application among the plurality of remote applications, and the first remote application being associated with the processing plug-in,
  wherein
    the anonymized data record is configured to be used as input data by the first remote application,
    the cloud data repository includes a plurality of sub-repositories, each of the plurality of remote applications being configured to access a respective sub-repository among the plurality of sub-repositories, and
    the uploading uploads the anonymized data record to a first sub-repository among the plurality of sub-repositories, the first remote application being configured to access only the first sub-repository among the plurality of sub-repositories.

2. The method of claim 1, wherein
  the medical data record is received via the core module, and the method further comprises:
  selecting the processing plug-in from among the available plug-ins via the core module, the selecting being based on the medical data record.

3. The method of claim 2, wherein the anonymized data record is configured to be used as input data by the first remote application.

4. The method of claim 2, wherein
  the medical data record includes a first data item and a second data item, the first data item including personal data related to a patient; and
  the anonymized data record includes the second data item and a data record identifier, the data record identifier being based on the first data item.

5. The method of claim 4, further comprising:
  applying an anonymization function of the core module on the first data item to obtain the data record identifier.

6. The method of claim 5, wherein the data record identifier is based on an anonymization level parameter provided to the anonymization function.

7. The method of claim 2, further comprising:
  processing other data via the processing plug-in during the uploading; and
  notifying, via the core module, the processing plug-in about completion of the uploading.

8. The method of claim 2, further comprising:
  notifying the first remote application about completion of the uploading by sending a notification message to the first remote application via the core module.

9. The method of claim 2, further comprising:
  receiving a plug-in installation file via the core module, the plug-in installation file including an installable plug-in and a configuration file; and
  installing the installable plug-in as an additional available plugin via the core module, the installing being based on the configuration file.

10. The method of claim 2, further comprising:
  determining a resource parameter of a local transmission unit hosting the local transmission software, the resource parameter being based on at least one of memory usage or processor usage of the local transmission unit;
  initializing a process of a first plug-in among the available plug-ins in response to determining the resource parameter is below a first resource threshold; and
  terminating a process of a second plug-in among the available plug-ins in response to determining the resource parameter is above a second resource threshold.

11. The method of claim 2, further comprising:
  receiving a message from the first remote application via the local transmission software, the message indicating storage of a processed data record in the cloud data repository, the processed data record being generated via the first remote application based on the anonymized data record;
  downloading the processed data record from the cloud data repository via the processing plug-in; and
  storing the processed data record within a local data repository via the processing plug-in.

12. The method of claim 1, wherein
  the medical data record includes a first data item and a second data item, the first data item including personal data related to a patient; and the anonymized data record includes the second data item and a data record identifier, the data record identifier being based on the first data item.

13. The method of claim 12, further comprising:
applying an anonymization function of the core module on the first data item to obtain the data record identifier.

14. The method of claim 13, wherein the data record identifier is based on an anonymization level parameter provided to the anonymization function.

15. The method of claim 1, further comprising:
processing other data via the processing plug-in during the uploading; and
notifying, via the core module, the processing plug-in about completion of the uploading.

16. The method of claim 1, further comprising:
notifying the first remote application about completion of the uploading by sending a notification message to the first remote application via the core module.

17. The method of claim 1, further comprising:
receiving a plug-in installation file via the core module, the plug-in installation file including an installable plug-in and a configuration file; and
installing the installable plug-in as an additional available plugin via the core module, the installing being based on the configuration file.

18. The method of claim 1, further comprising:
determining a resource parameter of a local transmission unit hosting the local transmission software, the resource parameter being based on at least one of memory usage or processor usage of the local transmission unit;
initializing a process of a first plug-in among the available plug-ins in response to determining the resource parameter is below a first resource threshold; and
terminating a process of a second plug-in among the available plug-ins in response to determining the resource parameter is above a second resource threshold.

19. The method of claim 1, further comprising:
receiving an action message from one of the plurality of remote applications via the core module, the action message including a plug-in identifier;
transmitting the action message via the core module to a receiving plug-in among the available plug-ins, the receiving plug-in being selected by the core module based on the plug-in identifier; and
processing the action message via the receiving plug-in.

20. The method of claim 1, further comprising:
receiving a message from the first remote application via the local transmission software, the message indicating storage of a processed data record in the cloud data repository, the processed data record being generated via the first remote application based on the anonymized data record;
downloading the processed data record from the cloud data repository via the processing plug-in; and
storing the processed data record within a local data repository via the processing plug-in.

21. A non-transitory computer program product storing a local transmission software, the local transmission software being loadable into a storage unit of a local transmission unit and including program code sections that, when executed by a calculation unit of the local transmission unit, cause the local transmission unit to perform the method of claim 1.

22. A non-transitory computer-readable medium storing program code sections of a local transmission software that, when executed by a local transmission unit cause the local transmission unit to execute the method of claim 1.

23. A local transmission unit configured to host a local transmission software for uploading a data record to a cloud data repository, the local transmission unit comprising:
a calculation unit; and
a memory, the local transmission software including a core module and available plug-ins, each available plug-in among the available plug-ins being associated with a respective remote application among a plurality of remote applications, and the plurality of remote applications being configured to access a cloud data repository, wherein the calculation unit is configured to execute the local transmission software to cause the local transmission unit to
receive a medical data record,
generate an anonymized data record based on the medical data record via a processing plug-in among the available plug-ins, and
upload the anonymized data record to a cloud data repository via the core module, the anonymized data record in the cloud data repository being accessible via a first remote application among the plurality of remote applications, and the first remote application being associated with the processing plug-in,
wherein
the anonymized data record is configured to be used as input data by the first remote application,
the cloud data repository includes a plurality of sub-repositories, each of the plurality of remote applications being configured to access a respective sub-repository among the plurality of sub-repositories, and
the calculation unit is configured to execute the local transmission software to cause the local transmission unit to upload the anonymized data record to a first sub-repository among the plurality of sub-repositories, the first remote application being configured to access only the first sub-repository among the plurality of sub-repositories.

24. The local transmission unit of claim 23, wherein the calculation unit is configured to execute the core module to cause the local transmission unit to:
receive the medical data record; and
select the processing plug-in from among the available plug-ins based on the medical data record.

* * * * *